(12) United States Patent
Duan et al.

(10) Patent No.: US 7,991,510 B2
(45) Date of Patent: Aug. 2, 2011

(54) FLOW MEASUREMENT AND CONTROL WITH BUBBLE DETECTION

(75) Inventors: Hao Duan, Huntington Beach, CA (US); Aaron S. Tint, Rowland Heights, CA (US); Christophe Ellec, Corona, CA (US)

(73) Assignee: Brooks Instrument, LLC, Hatfield, PA (US)

( * ) Notice: Subject to any disclaimer, the term of this patent is extended or adjusted under 35 U.S.C. 154(b) by 182 days.

(21) Appl. No.: 12/405,007

(22) Filed: Mar. 16, 2009

(65) Prior Publication Data

US 2009/0281671 A1   Nov. 12, 2009

Related U.S. Application Data

(63) Continuation of application No. 11/503,873, filed on Aug. 11, 2006, now abandoned.

(60) Provisional application No. 60/707,628, filed on Aug. 12, 2005.

(51) Int. Cl.
*G06F 19/00* (2011.01)

(52) U.S. Cl. .................................... 700/282; 700/283

(58) Field of Classification Search .............. 700/282, 700/283; 422/68, 58; 210/87; 604/65, 123; 702/84

See application file for complete search history.

(56) References Cited

U.S. PATENT DOCUMENTS

| | | | | |
|---|---|---|---|---|
| 5,584,806 A | * | 12/1996 | Amano | 604/65 |
| 5,868,710 A | * | 2/1999 | Battiato et al. | 604/123 |
| 6,280,408 B1 | * | 8/2001 | Sipin | 604/65 |
| 6,349,740 B1 | * | 2/2002 | Cho et al. | 137/487.5 |
| 6,516,675 B1 | * | 2/2003 | Jan et al. | 73/861.63 |
| 2005/0124929 A1 | * | 6/2005 | Katz et al. | 604/65 |
| 2006/0211981 A1 | * | 9/2006 | Sparks et al. | 604/44 |

* cited by examiner

*Primary Examiner* — Kidest Bahta
(74) *Attorney, Agent, or Firm* — SNR Denton US LLP

(57) ABSTRACT

Systems and methods for liquid flow sensing and control for use with a variety of different types of liquid flow measurement and control systems. The liquid flow sensor system senses a flow signal indicative of the flow rate of the liquid flowing in a sensor conduit and analyzes the flow signal to determine, by detecting characteristic changes in the signal, whether a bubble is present in the sensor conduit. Where the system determines that a bubble is present, it may generate an alarm signal indicative of the presence of the bubble. A flow control system incorporating the flow sensor as a feedback source may respond to the detection of a bubble by temporarily freezing the flow control parameters until the bubble has exited the sensor conduit. The flow control system can implement procedures for clearing a bubble from the sensor conduit where the system detects that the bubble has become stuck.

45 Claims, 16 Drawing Sheets

FLOW MEASUREMENT AND CONTROL WITH BUBBLE DETECTION

CROSS REFERENCE TO RELATED APPLICATIONS

This application claims priority under 35 U.S.C. §119(e) to U.S. Non Provisional application Ser. No. 11/503,873, filed Aug. 11, 2006, and from U.S. Provisional Patent Application No. 60/707,628, filed Aug. 12, 2005, entitled "Bubble Algorithm Design," which is incorporated herein by reference in its entirety.

BACKGROUND OF THE INVENTION

1. Field of Invention

The present invention relates to systems and methods for measuring and controlling liquid flow, and more specifically to systems and methods for measuring and controlling liquid flow in environments where bubbles may be present in the liquid flow.

2. Discussion of Related Art

Several techniques exist for measuring a flow rate of a liquid flowing in a conduit, pipe, or tube. These include thermal flow meters, coriolis force flow meters, differential pressure flow meters, and ultrasonic flow meters. Generally, liquid flow meters sense one or more parameters of the flow that can be calibrated to correspond to the rate (e.g., volumetric or mass) of flow of the liquid. Such flow meters can be used either as passive monitors of liquid flow through a system of interest (i.e., used as a flow meter), or as a sensor element in a closed-loop feedback system that controls liquid flow in the system of interest (i.e., as a flow meter in a flow rate controller).

SUMMARY OF INVENTION

When a bubble enters a sensor conduit of any type of flow meter, the signal upon which the flow meter bases its flow measurement may be disturbed. This can result in spurious measurements. Where the flow meter is operating as the sensor element of a closed-loop flow controller, the closed loop system may react to the spurious signal and attempt to compensate for what it interprets as a change in the flow rate of the liquid. This can lead to instability in the controlled flow, which interferes with the purpose of the controller to provide a stable flow at a rate corresponding to a (typically user-set) setpoint.

Although the presence of bubbles can affect any type of flow meter or controller (and to varying degrees), it is especially problematic for ultrasonic-type flow meters, particularly where such ultrasonic flow meters are used to measure or control relatively low flow rates (e.g., between 5 to 50 ml/min, or less). Applicants have recognized that conventional ultrasonic flow meters and flow controllers lack the ability to detect and respond to the presence of a bubble in a sensor conduit and to remain in a stable state despite the presence of the bubble in the sensor conduit, especially where they are used to measure and/or control such relatively low flow rates.

Applicants have developed systems and methods for achieving stable operation of liquid flow controls even when a bubble passes through the sensor system. The systems and methods developed by applicants can minimize the effect of the bubble on liquid flow measurements or on controlled liquid flow rates.

In exemplary embodiments, a liquid flow sensor system of the present invention senses a flow signal indicative of the flow rate of the liquid flowing in a sensor conduit. The system analyzes the flow signal to determine, for example, by detecting characteristic changes in the signal, whether a bubble is present in the sensor conduit. Where the system determines that a bubble is present, it may generate an alarm signal indicative of the presence of the bubble. In exemplary embodiments of a flow control system that incorporates the flow sensor as a feedback source for closed-loop control and includes bubble detection, the flow control system may respond to the detection of a bubble by temporarily freezing the flow control parameters until the bubble has exited the sensor conduit. In this way, the system may avoid instabilities in flow rate caused by the closed-loop flow control attempting to track spurious flow sensor signals caused by the presence of the bubble.

In accordance with an aspect of the present invention, a method of measuring a flow rate of a liquid flowing in a liquid flow sensor is provided, the liquid flow sensor including a sensor conduit and the liquid including a plurality of bubbles formed therein. The method comprises acts of repeatedly sensing a flow signal indicative of the flow rate of the liquid flowing in the sensor conduit; determining, based upon at least one parameter of the flow signal, whether at least one bubble is disposed in the liquid within the sensor conduit; providing, in response to a determination that no bubble is disposed in the liquid within the sensor conduit, a flow rate signal indicative of the flow rate of the liquid flowing in the liquid flow sensor based upon a most recently sensed flow signal; and providing, in response to a determination that the at least one bubble is disposed in the liquid within the sensor conduit, at least one of: a) a flow rate signal based upon the most recently sensed flow signal and an alert signal indicative of a presence of the at least one bubble, and b) a flow rate signal indicative of the flow rate of the liquid flowing in the liquid flow sensor based upon other than the most recently sensed flow signal.

In accordance with one embodiment wherein the liquid flow sensor comprises an ultrasonic liquid flow sensor, the at least one parameter of the flow signal comprises an ultrasonic flow signal amplitude. In accordance with this embodiment, the method may further comprise an act of calculating, responsive to the act of repeatedly sensing, a weighted sum, such as a running average, of a value of the ultrasonic flow signal amplitude, wherein the act of determining includes an act of determining whether a most recently sensed value of the ultrasonic flow signal amplitude deviates from the weighted sum by more than a determined amount.

In accordance with another embodiment wherein the liquid flow sensor comprises an ultrasonic liquid flow sensor, and wherein the flow signal comprises an ultrasonic time-of-flight difference flow signal, the at least one parameter of the flow signal includes a magnitude of the ultrasonic time-of-flight difference flow signal. In accordance with a further embodiment, the act of determining includes an act of determining whether the magnitude of the ultrasonic time-of-flight difference flow signal deviates from the magnitude of a prior ultrasonic time-of-flight difference flow signal by more than a threshold value. In accordance with a still further embodiment of the present invention, the magnitude of the ultrasonic time-of-flight difference flow signal may be used in combination with detection of a bubble based upon the ultrasonic flow signal amplitude to provide early detection of the presence of a bubble in the sensor conduit.

In accordance with another aspect of the present invention, a method of controlling the flow rate of a liquid through a flow conduit that is coupled to a controllable valve and a liquid flow sensor is provided. The liquid flow sensor includes a sensor conduit and the liquid includes a plurality of bubbles formed therein, and the method comprises acts of repeatedly sensing a flow signal indicative of the flow rate of the liquid flowing in the sensor conduit; determining, based upon at least one parameter of the flow signal, whether at least one bubble is disposed in the liquid within the sensor conduit; providing, in response to a determination that no bubble is disposed in the liquid within the sensor conduit, control parameters for the controllable valve based upon the most recently sensed flow signal; providing, in response to a determination that the at least one bubble is disposed in the liquid within the sensor conduit, control parameters for the controllable valve based upon other than the most recently sensed flow signal; and controlling the controllable valve according to the control parameters.

In accordance with one embodiment, the method further includes an act of calculating, responsive to the act of repeatedly sensing, a weighted sum, such as a running average, of a value of the at least one parameter of the flow signal, wherein the act of determining includes an act of determining whether a most recently sensed value of the at least one parameter of the flow signal deviates from the weighted sum by more than a determined amount. In accordance with another embodiment, the act of providing control parameters based upon other than the most recently sensed flow signal includes providing the most recently provided control parameters for which it was previously determined that no bubble was disposed in the liquid within the sensor conduit.

In accordance with yet a further embodiment, the method further comprises acts of waiting a predetermined period of time in response to a determination that the at least one bubble is disposed in the liquid within the sensor conduit, determining, after the predetermined period of time, whether the at least one bubble is still disposed in the liquid within the sensor conduit, based upon the at least one parameter of the flow signal, and executing, in response to a determination that the at least one bubble is still disposed in the liquid within the sensor conduit, a controlled force procedure to remove the at least one bubble from the liquid within the sensor conduit. In one embodiment, the controlled force procedure includes opening and shutting the controllable valve.

In accordance with a further aspect of the present invention, a system for measuring a flow rate of a liquid flowing in a flow conduit is provided for a liquid that may include a plurality of bubbles formed therein. The system comprises a liquid flow sensor that includes a sensor conduit fluidly coupled to the flow conduit and a bubble detection module. The liquid flow sensor is configured to sense a flow rate of the liquid flowing in the sensor conduit and provide a flow signal indicative of the flow rate of the liquid flowing in the sensor conduit. The bubble detection module is coupled to the liquid flow sensor to receive the flow signal and determine, based upon at least one parameter of the flow signal, whether at least one bubble is disposed in the liquid within the sensor conduit. The bubble detection module is configured to provide, in response to a determination that no bubble is disposed in the liquid within the sensor conduit, a flow rate signal indicative of the flow rate of the liquid flowing in the liquid flow sensor based upon a most recently sensed flow signal, and to provide, in response to a determination that the at least one bubble is disposed in the liquid within the sensor conduit, at least one of: a) a flow rate signal based upon the most recently sensed flow signal and an alert signal indicative of a presence of the at least one bubble, and b) a flow rate signal indicative of the flow rate of the liquid flowing in the liquid flow sensor based upon other than the most recently sensed flow signal.

In accordance with one embodiment directed to a flow controller, the system further comprises a controllable valve in fluid communication with the flow conduit, to control the flow rate of the fluid flowing in the flow conduit based upon control parameters provided to the controllable valve, and a controller, coupled to the liquid flow sensor and the controllable valve, to receive the flow signal from the liquid flow sensor and provide the control parameters to the controllable valve. In accordance with one embodiment, the bubble detection module is implemented in the controller, wherein, upon the determination that no bubble is disposed in the liquid within the sensor conduit, the controller provides the control parameters to the controllable valve based upon the most recently sensed flow signal, and wherein, upon a determination that the at least one bubble is disposed in the liquid within the sensor conduit, the controller provides the control parameters to the controllable valve based upon other than the most recently sensed flow signal.

In an alternative embodiment directed to a flow controller, wherein the bubble detection module provides the flow rate signal based upon the most recently sensed flow signal and the alert signal indicative of the presence of the at least one bubble in response to the determination that the at least one bubble is disposed in the liquid within the sensor conduit, the system further comprises a controllable valve in fluid communication with the flow conduit, to control the flow rate of the fluid flowing in the flow conduit based upon control parameters provided to the controllable valve, and a controller, coupled to the bubble detection module, to receive the flow rate signal and the alert signal and provide the control parameters to the controllable valve. In a further embodiment, in response to the alert signal, the controller freezes the control parameters provided to the controllable valve at a prior value. In yet another embodiment, in response to the alert signal, the controller is configured to wait for a predetermined period of time, and upon a determination that the at least one bubble is still disposed in the liquid within the sensor conduit and the predetermined period of time has elapsed, implement a controlled force procedure to remove the at least one bubble from the liquid within the sensor conduit.

BRIEF DESCRIPTION OF DRAWINGS

Exemplary embodiments of systems and methods according to the present invention will be understood with reference to the accompanying drawings, which are not intended to be drawn to scale. In the drawings, each identical or nearly identical component that is illustrated in various figures is represented by a like designator. For purposes of clarity, not every component may be labeled in every drawing. In the drawings.

DETAILED DESCRIPTION

Figure 1:
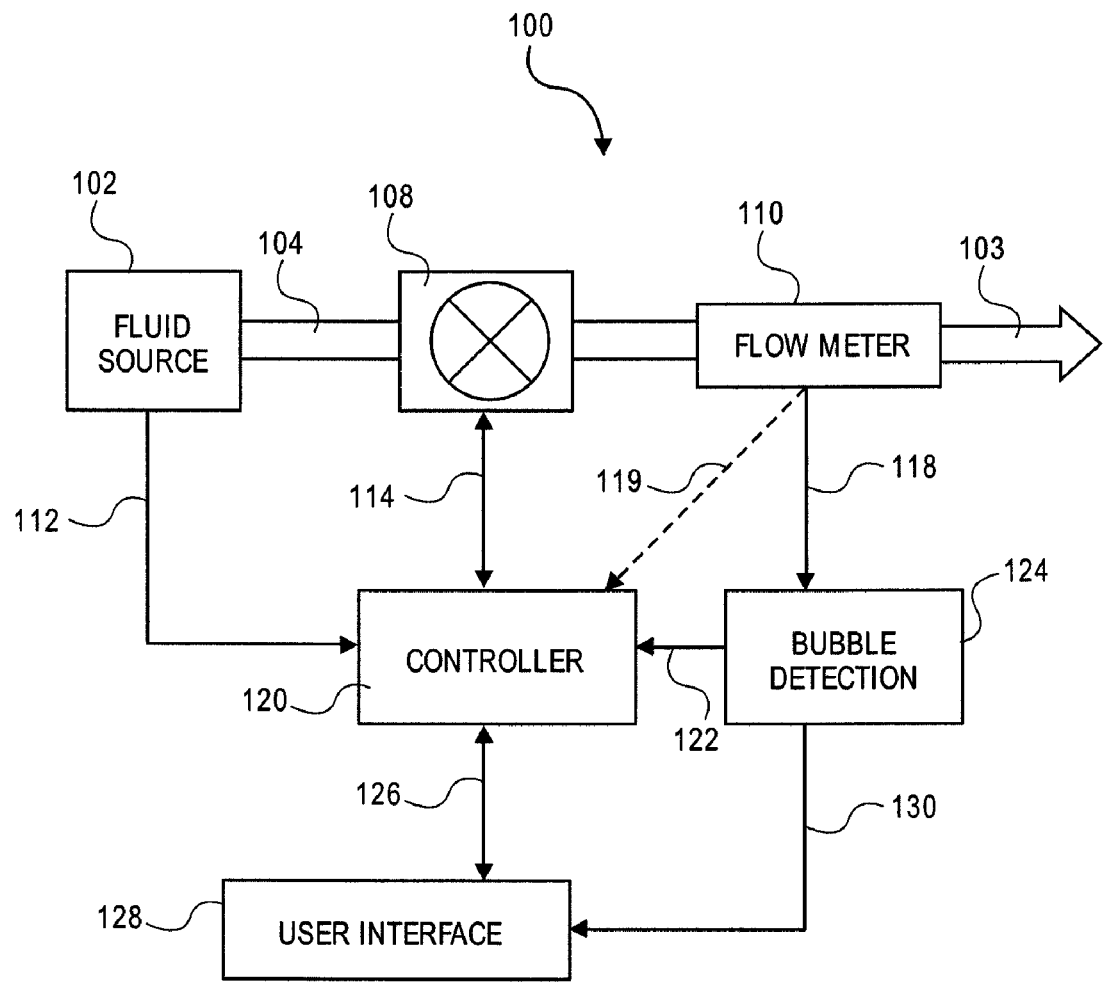
FIG. 1 is a schematic representation of an exemplary embodiment of a liquid flow measurement and/or control system.

Referring to FIG. 1, there is illustrated a schematic block-diagram of one example of a liquid control system according to aspects of the present invention. The system 100 as illustrated includes a controllable valve 108 through which liquid flows, as indicated by line/arrow 104. It is to be appreciated that although the following discussion will refer primarily to element 108 being a controllable or variable valve, element 108 may also be another type of liquid actuator such as, for example, a pump. The valve 108 may be, for example, an electronically controlled variable valve that may be adjusted to vary the flow rate of the liquid through the system. The valve 108 is controlled by a controller 120 as indicated by line 114. The controller 120 may be, for example, a microprocessor-based controller. A liquid flow meter 110 may be positioned downstream of the valve 108, as shown. Alternatively, the liquid flow meter 110 may be disposed upstream of the valve 108. The flow of the liquid may be measured by the flow meter 110 that may communicate with the controller 120, either directly via line 119, or indirectly as indicated by lines 118 and 122. As illustrated in FIG. 1, in one example, the flow meter 110 may be integral to the liquid line 104, such that liquid flowing in the liquid line 104 also flows through the flow meter 110. It is to be appreciated that the flow meter 110 may be integral with the liquid line 104, or may be positioned in a branch or bypass liquid line such that the flow meter 110 may measure only a portion of the entire liquid stream.

In a conventional liquid flow control system, signals from the flow meter indicative of the liquid flow rate may be sent to controller 120, and the controller 120 may be adapted to use information, such as the flow rate of the liquid, provided by the flow meter 110 to monitor the flow rate of the liquid and to control the valve 108 to achieve a desired rate of flow, thereby providing closed-loop control of the liquid flow in the system 100. For example, in one embodiment, control of the liquid flow rate is achieved by a control system in which the liquid flow meter 110 is a feedback element in a closed loop system. The flow meter 110 produces an electronic signal indicative of the rate of flow of the liquid through the liquid line 104. The flow meter signal may provide real-time feedback of liquid flow and may be input to the controller 120. A signal provided by the controller 120 is input to an actuator driving the valve 108 (as indicated by line 114) and may be used to control the valve 108 so as to vary the rate of flow as required to achieve the desired rate of liquid flow. The desired liquid flow rate may also be an input parameter to the controller 120. For example, the liquid may enter the illustrated portion of the system 100 from a source 102 which may be, for example, an upstream element in the system 100, a storage element, and the like. The source 102 may also include sensors that may provide information to the controller 120, as indicated by line 112, such as set-points and limits of the amount of liquid available, temperature, pressure, concentration, density, etc., and possibly an initial flow rate of the liquid. The controller 120 may be adapted to use such information, and other inputs, to adjust the flow rate of liquid in liquid line 104.

In an exemplary embodiment of a flow control system according to the present invention, a bubble detection module 124 may analyze one or more signals provided by the flow meter as represented by line 118. The bubble detection module 124 may then pass information to the controller 120 as illustrated by line 122. The information passed to controller 120 may include the current flow meter signal 118, one or more prior flow meter signals, and/or an alert signal (such as a Boolean flag) indicative of the presence or absence of a bubble in the flow meter 110. Although the bubble detection module 124 is illustrated in FIG. 1 as a distinct module, in other embodiments it may be incorporated into the flow meter 110, or into the controller 120. Where the bubble detection module 124 is incorporated into the flow meter 110 it may analyze the flow meter signal for the presence of a bubble prior to passing information to the controller. In embodiments in which the bubble detection module is incorporated into the controller 120, it may analyze the incoming signal from the flow meter 118 for the presence of a bubble so that the controller may respond accordingly as described in more detail further below.

In addition, as illustrated in FIG. 1, the controller 120 may be coupled to a user interface 128 which may be, for example, a graphically based user interface. The user interface 128 may allow a user to monitor the system and to provide input to the controller 120, as indicated by line 126. The user may be able, via the user interface 128, to observe parameters of the system (provided by the controller 120 or by the flow meter 110) and/or to provide inputs to the controller 120 such as, for example, a desired flow rate of the liquid, (i.e., liquid flow rate set points) and/or upper and lower flow rate limits. The controller 120 may output to the user interface 128 various information including, for example, actual flow rate, out-of-limit alarms, and data management and data decision support information. It should be appreciated that the controller 120 may be coupled to another system computer instead of, or as well as, being coupled to the user interface 128. The bubble detection module 124 may also be coupled to user interface 128, as illustrated schematically by line 130. Thus, for example, the user interface 128 may respond to receipt from the bubble detection module 124 of a positive alert signal indicative of the presence of a bubble by displaying an alert. In embodiments in which the bubble detection module is incorporated into the flow meter 110 or the controller 120, the user interface may receive the bubble alert status directly from the flow meter 110 or the controller 120.

It is to be appreciated that the controller 120 may be programmed with one of a variety of programs for controlling the valve 108. For example, the controller may be programmed to utilize proportional integral (PI) control, proportional integral differential (PID) control, etc., such as, for example, described in detail in connection with a thermal mass flow meter/controller in commonly-owned U.S. Pat. No. 6,962,164, which is herein incorporated by reference in its entirety. In another example, the controller may be adapted to use a "model-free" adaptive control algorithm to drive the valve 108. This method includes a feedback "neuron-based" control algorithm that is independent of the particular liquid flowing in the system and does not require a priori knowledge of the dynamics of the system. At least one embodiment of this method is described in detail in U.S. Pat. No. 6,684,112 to George Shu-Xing Cheng, which is herein incorporated by reference in its entirety.

According to one embodiment, the flow meter 110 may be an ultrasonic flow meter that is adapted to use parameters of ultrasonic waves propagated through the liquid to determine the flow rate of the liquid. Such parameters may include the amplitude, frequency, and/or the time-of-flight of ultrasonic signals propagating through the liquid. Illustrative examples of the manner in which ultrasonic signals may be used to determine the flow rate of a liquid are described, for example, in commonly owned U.S. application Ser. No. 10/878,974 entitled "Ultrasonic Liquid Flow Controller," published as US20050288873A1, which is herein incorporated by reference in its entirety. In other embodiments, other types of flow meters may be employed, including without limitation coriolis force flow meters, thermal flow meters, or other flow meters known in the art.

Figure 2:
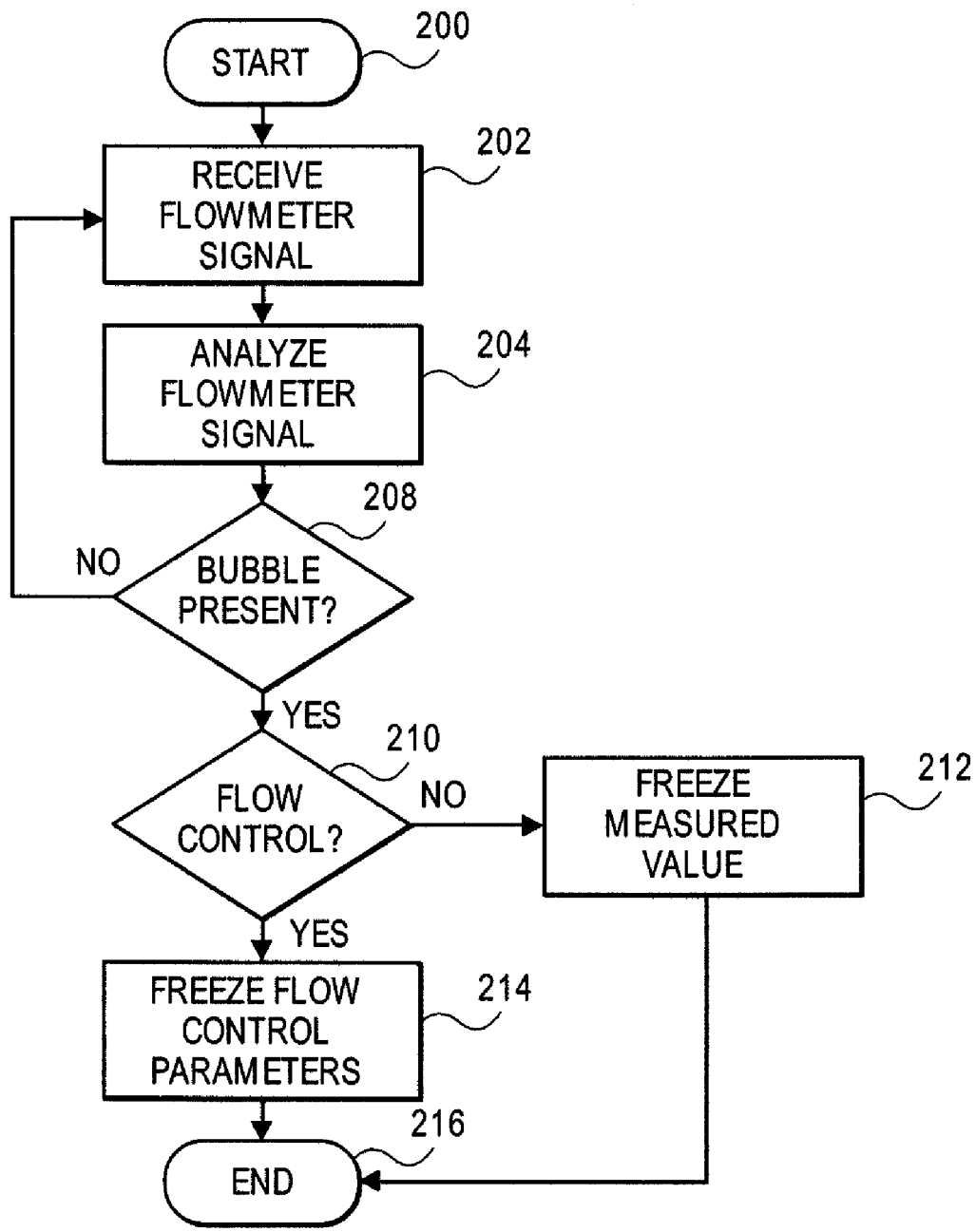
FIG. 2 is a flow diagram illustrating an exemplary embodiment of a method of detecting and responding to the presence of a bubble in the sensor conduit of a liquid flow measurement and/or control system.

FIG. 2 is a flow diagram functionally illustrating, in broad overview, an exemplary method that may be performed by a flow meter and/or flow controller system to detect and respond to the presence of a bubble in a sensor conduit. The system may begin (block 200) at startup or with input from a user, for example, initiating flow control. In an exemplary embodiment, the system periodically measures the flow through the flow meter, receiving a flow meter signal (block 202). The nature of the flow meter signal will depend upon the type of flow meter used in the system. The received flow meter signal may be either a raw signal from the flow meter, a calibrated signal corresponding to the liquid flow rate in the system as a whole, or some combination of raw signal parameters and calibrated measurements. In some embodiments, the received flow meter signal may be recorded or stored in a memory associated with the controller 120, the flow meter 110, or the bubble detection module 124.

In block 204, the system analyzes the flow meter signal and determines whether the signal indicates that a bubble is present in the sensor conduit of the flow meter (block 208). The presence of a bubble can interfere with the flow meter signal in characteristic ways that make it possible to analyze the flow meter signal (or the evolution of flow meter signal parameters over time) to detect a bubble's entry into and/or exit from the sensor conduit. Examples of such characteristic changes in the flow meter signal are discussed further below.

Where the analysis of the flow meter signal or of a number of received flow meter signals indicates that a bubble is present in the sensor conduit, an exemplary system may respond in a variety of ways, depending upon whether the flow meter and bubble detection system are deployed as part of a flow control system such as that illustrated in FIG. 1, or are being used to display, record, or log measurements of parameters of the liquid flow through the system (block 210). Where the flow meter is being used to display, record, or log measurements of liquid flow, then upon detection of a bubble, the system may provide a flow rate signal that is based upon one or more flow rate signals recorded prior to the detection of the bubble. For example, the system may freeze the displayed, recorded, or logged value at the last flow rate measured prior to detection of a bubble, or at an average of some fixed number of flow rate measurements taken prior to the detection of the bubble (block 212). In this way, spurious readings of flow rate that occur as a result of the bubble's disruption of the operation of the flow meter will not be displayed or recorded. Instead of or in addition to freezing the flow rate (block 212), the flow meter may also generate an alert signal that can be used to notify a user and/or other parts of the system that a bubble has been detected (and, therefore, that any flow rate measurements provided during the presence of the bubble may not be accurate). For example, the alert signal may be a Boolean flag that can be set and passed to the controller (e.g., as a separate signal or as a part of the signal 122 in FIG. 1) and/or to the user interface (i.e., signal 130 in FIG. 1) and/or written to a measurement log.

Where the flow meter and bubble detection system are incorporated into a flow control system (i.e., Flow Control YES), then the system may respond to the detection of a bubble in the sensor conduit by freezing the flow control parameters by which the controller 120 controls the controllable valve 108 (block 214). In this way, instead of the flow controller tracking and responding to spurious flow meter signals caused by the presence of a bubble in the sensor conduit, stable flow can be maintained while the bubble is present. Freezing the control parameters (block 214) can be achieved in a variety of ways. In one exemplary embodiment, the controller 120 receives from the bubble detection module 124 a positive alert signal indicating the presence of a bubble, and freezes the control parameters (such as the controllable valve setting) in response to that signal. In other embodiments (including embodiments in which the bubble detection module 124 is integral with the flow meter 110), the control parameters may be effectively frozen by providing to the controller 120 a fixed flow meter signal, for example, based upon a prior flow meter signal. In an embodiment in which the controller 120 computes control parameters based upon the flow meter signal it receives, it will not alter the control parameters as long as it is receiving a fixed flow meter signal. This fixed flow meter signal may be the last flow meter signal collected prior to detection of a bubble. Alternatively, the fixed flow meter signal may be a weighted sum (such as an average) of a number of prior recorded flow meter signals, or, it may be any fixed flow meter signal that is suitable to stabilize the controller response (and hence the flow through conduit 104) while a bubble is present in a sensor conduit.

Figure 3:
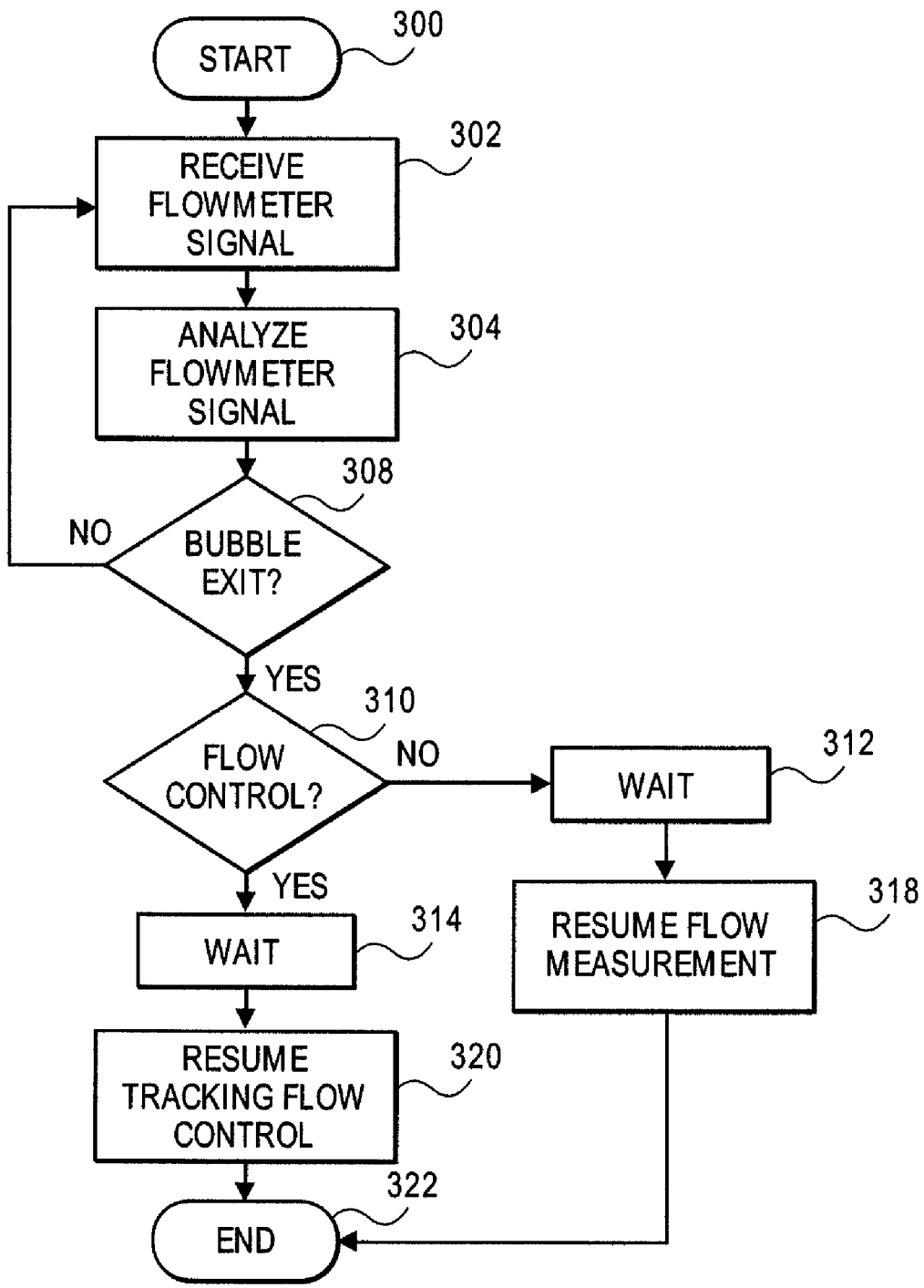
FIG. 3 is a flow diagram illustrating an exemplary embodiment of a method of detecting and responding to the exit of a bubble from the sensor conduit of a liquid flow measurement and/or control system.

FIG. 3 is a flow diagram illustrating the response of an exemplary embodiment of a flow meter or flow controller system to the bubble's exit from the sensor conduit. Having frozen the control parameters and/or the flow measurement upon detection of a bubble in block 214 (FIG. 2), an exemplary system may now await detection of flow meter signals characteristic of the bubble's exit from the sensor conduit (block 300). The system may periodically record signals from the flow meter (block 302) and analyze these signals (block 304) for features characteristic of a bubble's exit from the sensor conduit. As in the case of detecting the bubble's presence in the sensor conduit, the system may analyze the flow meter signal, a collection of a number of recorded flow meter signals, and/or the time evolution of flow meter signal parameters in order to detect changes characteristic of a bubble's exit from the sensor conduit as discussed in further detail below. The system may respond in a number of different ways to detection of the bubble's exit (step 308), depending upon whether the flow meter and bubble detection system are deployed as part of a flow control system such as that illustrated in FIG. 1, or are being used passively to display, record, or log measurements of liquid flow through the system (block 310). In an exemplary embodiment in which the flow meter and bubble detection system are being used to display, record, or log measurements of liquid flow, upon detection of the bubble's exit the system may simply resume the display, recording, or logging of new measurement values (block 318). In some embodiments, the flow meter system may (in addition to or instead of resuming display or recording of measurements) reset the alarm signal and/or send a signal indicating the absence of a bubble. Such a signal may be received by, for example, the user interface 128 and/or the controller 120.

In embodiments in which the flow meter and bubble detection system are incorporated into a flow control system, the system may respond to the detection of a bubble's exit from the sensor conduit by resuming flow control, i.e. allowing the controller 120 to alter the flow control parameters in response to flow meter signals (block 320). This can be achieved in a variety of ways. In one exemplary embodiment, the controller 120 receives from the bubble detection module 124 a signal indicating the exit of the bubble (e.g., the negation of the alarm signal generated in response to detection of a bubble), and in response to that signal resumes dynamic flow control. In other embodiments (including embodiments in which the bubble detection module 124 is integral with the flow meter 110), the control parameters may be effectively unfrozen by resuming the provision of current flow meter signals from the flow meter 110 to the controller 120.

In either case—whether the flow meter and bubble detection system are deployed as part of a flow control system such as that illustrated in FIG. 1, or are being used passively to display, record, or log measurements of liquid flow through the system—the system may include a delay between the detection of the bubble's exit and the resumption of dynamic flow control and/or display or recordation of measurements (blocks 312, 314). Such a delay may be useful to allow any disruption of the flow meter signal, flow rate, or of smooth, laminar flow caused by the bubble's passage through the sensor conduit to subside before resuming the recording of measurements or before resuming dynamic flow control.

Thus, in an exemplary embodiment, in response to detection of the bubble's exit from the sensor conduit (block 308), a countdown may be started for a predetermined amount of time (or, in the case of a digital control loop, a predetermined number of process or thread cycles), and the suspended flow meter measurements and/or controller parameters may be extended until the countdown is over. This delayed latching allows any spurious signals to subside before resuming measurement and/or flow control after the bubble clears the sensor conduit. In an exemplary embodiment the delay is optimized so as not to be so small that the spurious signals or flow turbulence may not yet have subsided, but also not to be so long that the flow parameters have an opportunity to drift away from the setpoint. In an exemplary embodiment, a delay of about 100-150 ms is sufficient to allow any spurious signals or flow turbulence to dissipate without unnecessarily delaying the resumption of real-time measurement and control, but longer delays may be necessary for some embodiments. The appropriate delay will depend upon the particular implementation of the flow meter and flow control system, including such parameters as flow rate, liquid viscosity, typical bubble size, the diameter or orientation of the sensor conduit, and others.

An exemplary flow meter or flow control system may also be adapted to respond to a second bubble entering the sensor conduit during the countdown process initiated by the exit of the first bubble. In one embodiment, where a second bubble enters the sensor conduit shortly after the exit of a first bubble, i.e., during the delay period represented by blocks 312 and/or 314, the resumption of flow meter measurements and/or controller parameters may be delayed further. Once the second bubble's exit is detected a new countdown may begin.

In alternative embodiments, instead of detecting the bubble's exit from the sensor conduit as described above, the flow meter and/or flow controller system may be configured to reset the alarm signal, resume measurement logging, and/or resume dynamic flow control after a preset amount of time or a preset number of process or thread cycles. An appropriate preset duration can be determined empirically, and may depend upon various system parameters, including such parameters as flow rate, liquid viscosity, typical bubble size, the diameter or orientation of the sensor conduit, and others.

In certain situations, for example where the flow is characterized by low flow rates and/or for low liquid pressures, a bubble may take a relatively long time to transit through the sensor conduit, causing a prolonged disruption of accurate flow parameter sensing. For that reason, some embodiments of flow controllers may include means for the controlled forcing of a bubble from the sensor conduit, particularly in instances where it appears that the bubble has become stuck. Controlled forcing typically involves temporarily altering the flow rate through the sensor conduit to urge the bubble out of the conduit. In an exemplary embodiment, the means for controlled forcing can include program code to rapidly open and close the valve in order to knock the bubble from the conduit.

In some embodiments, the controller may begin counting time and/or thread cycles upon detection of the presence of a bubble in the flow control system or upon receipt from the flow meter or the bubble detection module of an alarm signal indicating the presence of the bubble. In addition, the controller may be programmed or provided (e.g., through the user interface or other data source) with an expected transit time of a bubble through the sensor conduit. With that information, the system can respond with a controlled forcing procedure where the bubble's passage takes much longer than the expected transit time. The estimated transit time of a bubble can depend upon a variety of system parameters (such as liquid flow rate, viscosity, conduit diameter, etc.) and also upon the size of the bubbles that tend to occur in the system. For example, smaller bubbles move more slowly, as liquid tends to move around them rather than push them along the conduit. In contrast, larger bubbles tend to flow along with the liquid flow rate, but (depending upon the ratio of bubble size to conduit diameter) can be prone to becoming stuck in the conduit and/or causing unstable, turbulent, or slug flow. It should be appreciated that dependent on the orientation of the sensor conduit (e.g., whether the sensor conduit is disposed in a direction aligned with or transverse to a force of gravity or other force of acceleration) certain implementations may include a provision to detect and/or respond to a stuck bubble, while others may not.

In one exemplary embodiment, where a time larger than the expected transit time has passed without the system detecting the bubble's exit, the controller may, in response, execute a rapid opening and closing of the control valve, momentarily increasing the flow rate through the sensor conduit to force the bubble out. In such an embodiment, closed-loop operation may be suspended prior to executing this procedure and resumed thereafter, returning flow rate to its controlled level.

Where, after execution of a controlled forcing procedure, analysis of the flow meter signal indicates that the bubble is still within the flow conduit, the controlled forcing procedure may be repeated until a characteristically normal flow signal is achieved and/or the bubble-detection signals indicate that a bubble is no longer present.

Unlike a flow controller, a passive flow meter is not capable of forcing a blocked bubble out of a sensor conduit. In flow meter applications, a configurable alarm output may be used to signal an abnormal or disrupted flow condition where a bubble appears to have become stuck in the sensor conduit. In some embodiments, such a flag may be set and passed to a user interface, and/or recorded or logged along with measurements from the flow meter.

As described above, a bubble's presence in or exit from a sensor conduit can be detected by analysis of flow meter signal parameters for characteristic changes. An exemplary bubble detection system is now described.

One example of a flow controller that is known in the art employs an ultrasonic flow sensor to provide liquid flow rate feedback to the controller. Ultrasonic flow sensors measure liquid flow rate through a sensor conduit by propagating one or more ultrasonic signals through the liquid and measuring one or more effects that the flowing liquid can have on the propagating signals. For example, ultrasonic liquid flow sensors may detect changes in frequency, phase, or time of ultrasonic signals propagating through a flowing liquid to determine a transit time (time-of-flight) to measure flow rate. Such ultrasonic sensors and controllers incorporating them are described, for example, in U.S. Pat. Nos. 6,055,868, 5,974,897, and 3,575,050, as well as published application US2005/0288873A1.

Figure 10:
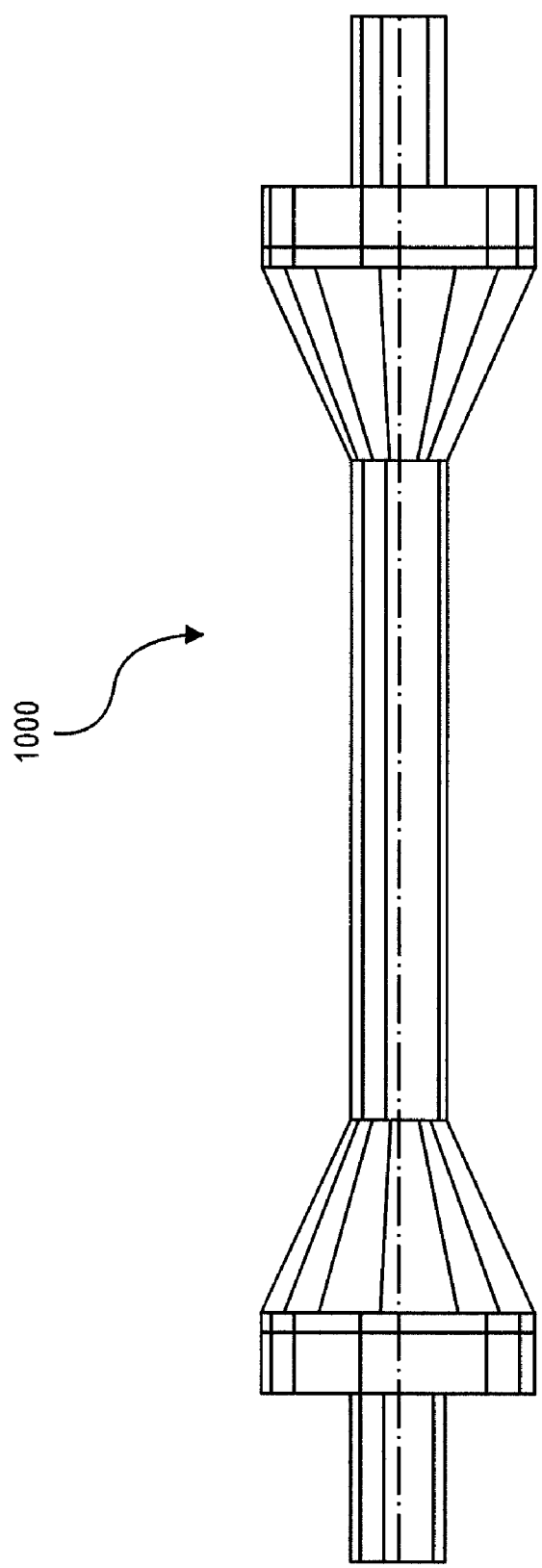
FIG. 10 illustrates an exemplary embodiment of an ultrasonic flow meter sensor conduit that may be used in accordance with the present invention.

An example of characteristic signals indicating the presence of a bubble in an exemplary ultrasonic flow sensor is illustrated in FIGS. 7A-7G. The ultrasonic flow sensor 700 includes a sensor conduit 712 and ultrasonic transducers 702 and 704. An alternative sensor conduit 1000 for use in an ultrasonic flow meter may have a different shape, such as that depicted in FIG. 10 and described in the commonly-owned, copending U.S. patent application entitled "Ultrasonic Flow Sensor" by Thomas Owen Maginnis and Kim Ngoc Vu, filed Ser. No. 11/502,308 on Aug. 10, 2006, and incorporated by reference herein. In the illustrated embodiment of FIG. 7A, liquid flows through the conduit 712 along flow direction 710. During operation, ultrasonic signals are generated at each of the transducers 702 and 704 and permitted to propagate through the flowing liquid for detection by the other transducer. The liquid flow rate can be determined from, for example, cross-correlation analysis of the frequency or phase, or the time difference of ultrasonic signals propagating along the flow direction 710 compared to those propagating against the flow direction 710 to establish a time-of-flight.

Figure 7A:
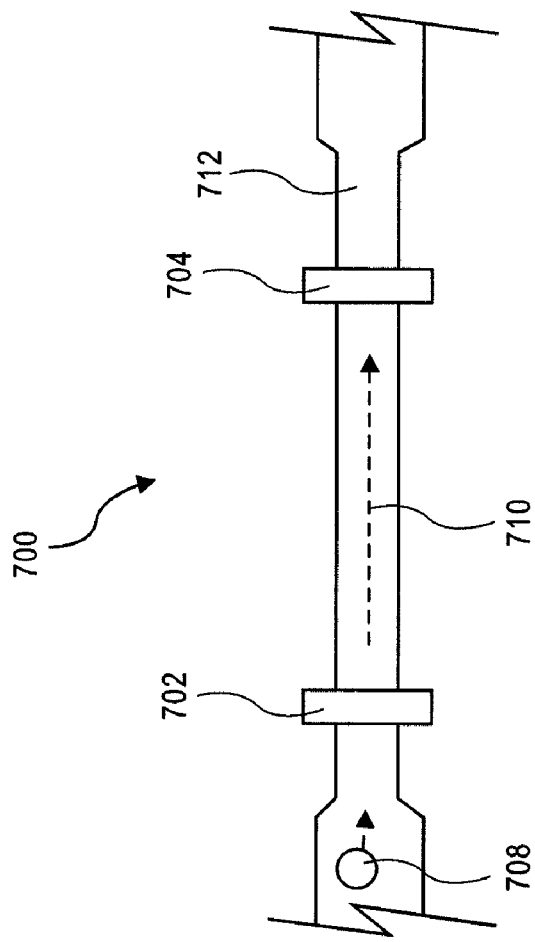
FIG. 7A illustrates a signal in an ultrasonic sensor conduit before a bubble enters the sensor conduit.
Figure 7A:
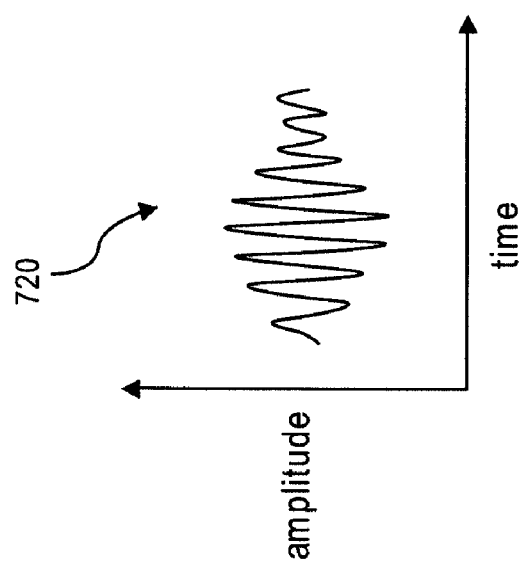

In an exemplary embodiment, a chirp signal such as that represented by reference number 720 in FIG. 7A is generated at transducer 702 and permitted to propagate through the liquid to transducer 704. Changes in its amplitude may be analyzed to determine whether a bubble 708 is present in the sensor conduit 712. These changes are shown schematically in FIGS. 7A-7G and are plotted schematically against time in FIG. 8. (Although this discussion considers the exemplary case in which the ultrasonic signal propagates along the flow direction, in some embodiments the chirp signal 720 is generated at transducer 704 and propagates upstream to transducer 702. In further embodiments, signals propagating in both directions are employed.)

Figure 7B:
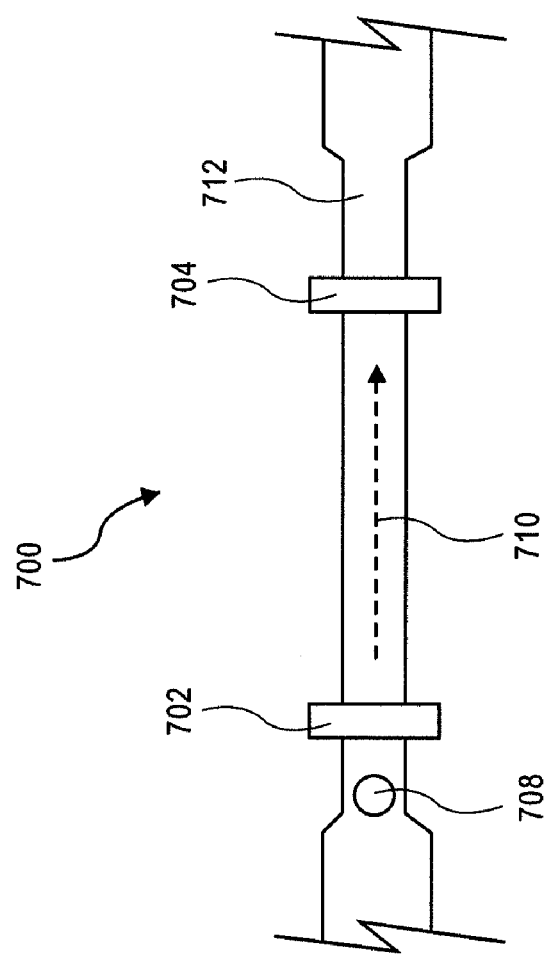
FIG. 7B illustrates a signal in an ultrasonic sensor conduit as a bubble reaches the entrance of the sensor conduit.
Figure 7B:
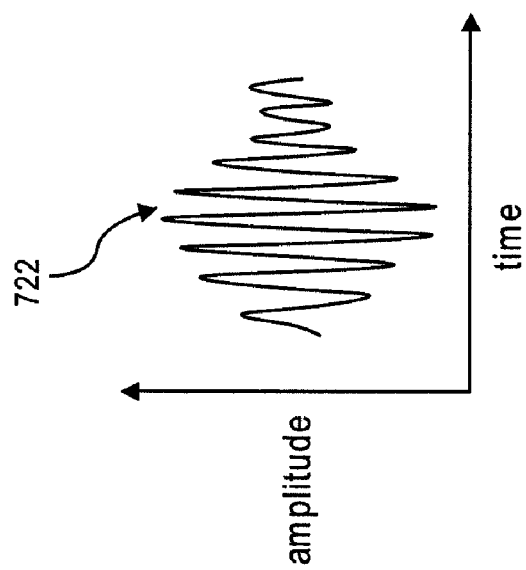
Figure 8:
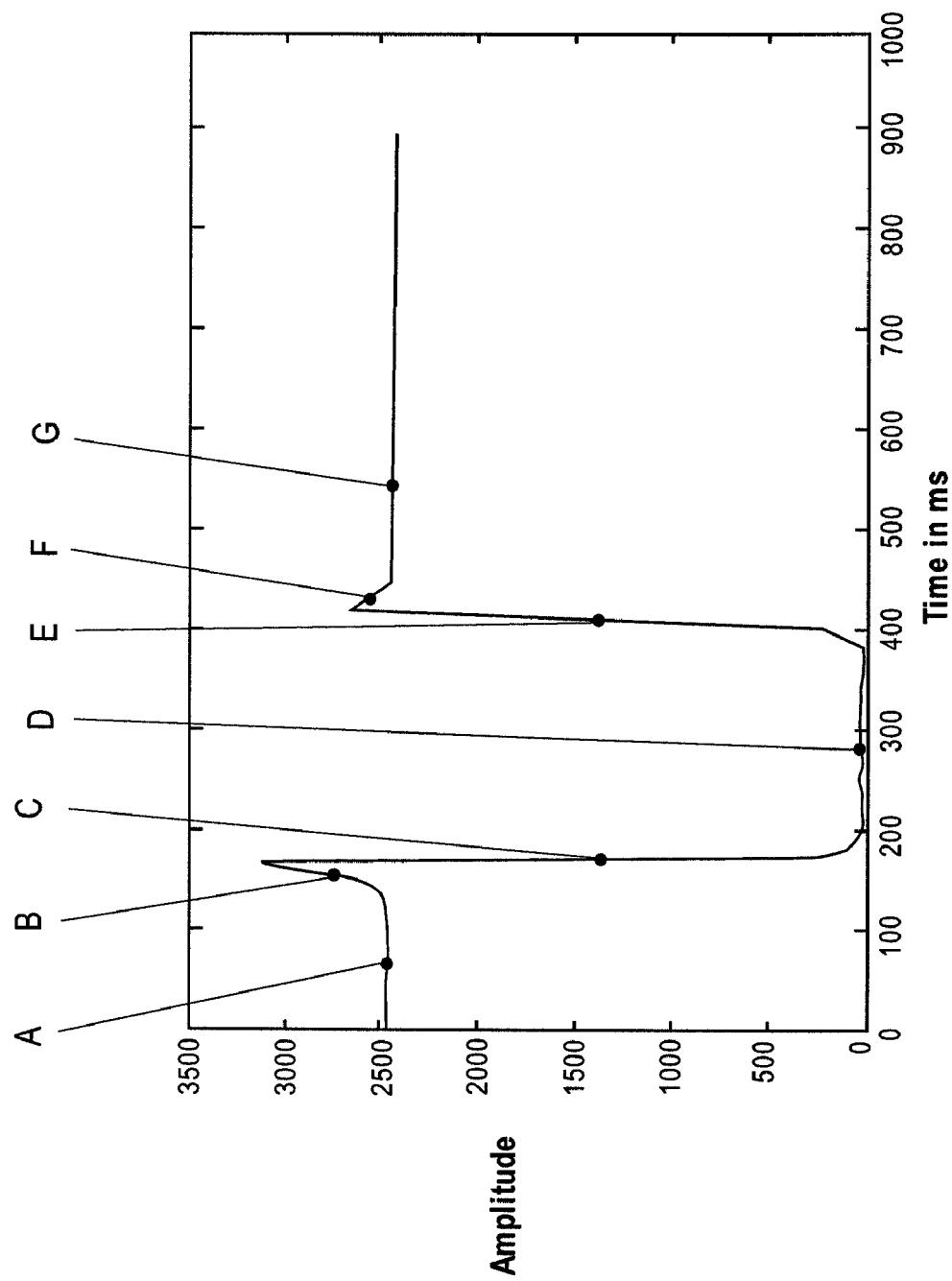
FIG. 8 illustrates an ultrasonic flow sensor signal plotted against time as a bubble traverses the sensor conduit of the flow sensor.

In FIG. 7A, before a bubble 708 enters the sensor conduit, the received signal amplitude is relatively steady with time (point A in FIG. 8). As the bubble 708 approaches the entrance to the measurement section of the sensor conduit, as shown in FIG. 7B, the amplitude of the received signal momentarily increases, as illustrated by reference number 722 in FIG. 7B and at point B in FIG. 8. This momentary increase in the amplitude of the received signal does not appear to be related to a change in the gain applied to received flow signal by the flow meter electronics (because it occurs over a period of time which is typically much smaller than the response time of the gain control in the flow meter electronics), and is believed to be attributable to the ultrasonic signals reflecting back from the bubble 708 at the entrance to the conduit 712 and reinforcing in phase with the transmitting wavefront that is traveling towards the direction of the transducer 704. Regardless of the physical mechanism, the observed change in signal amplitude is characteristic of the presence of a bubble, and thus can be used to detect the bubble.

Figure 7C:
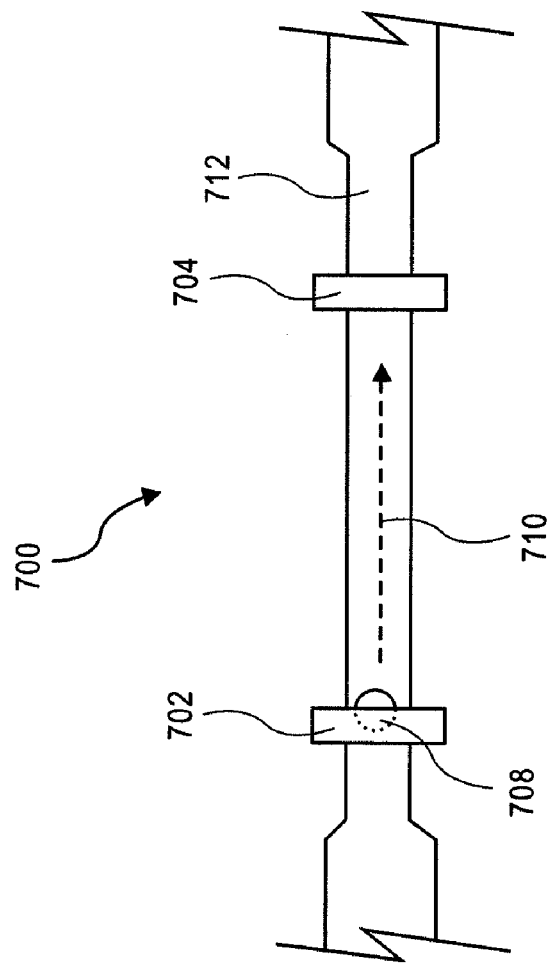
FIG. 7C illustrates a signal in an ultrasonic sensor conduit as a bubble passes a first transducer.
Figure 7C:
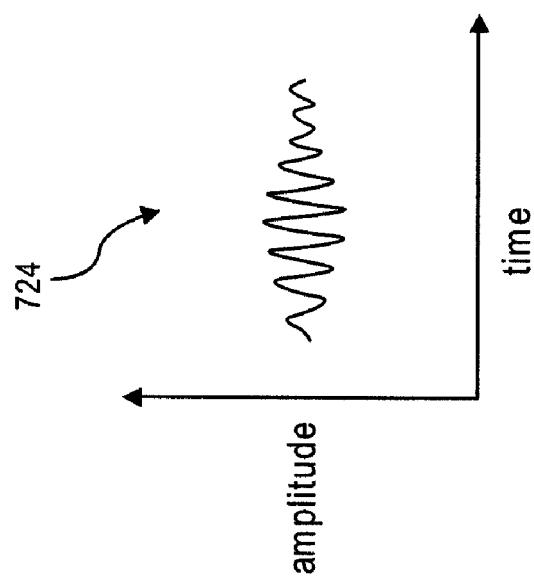
Figure 7D:
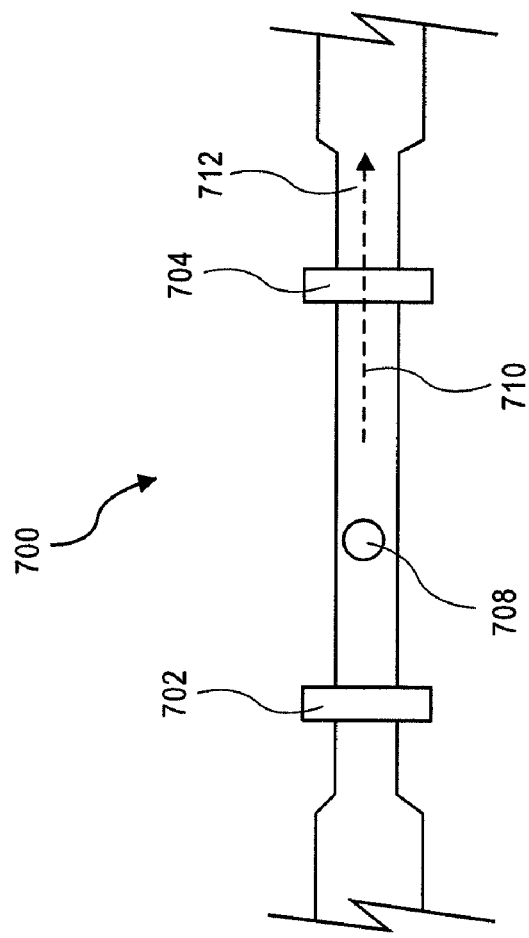
FIG. 7D illustrates a signal in an ultrasonic sensor conduit as a bubble traverses the middle of the conduit.
Figure 7D:
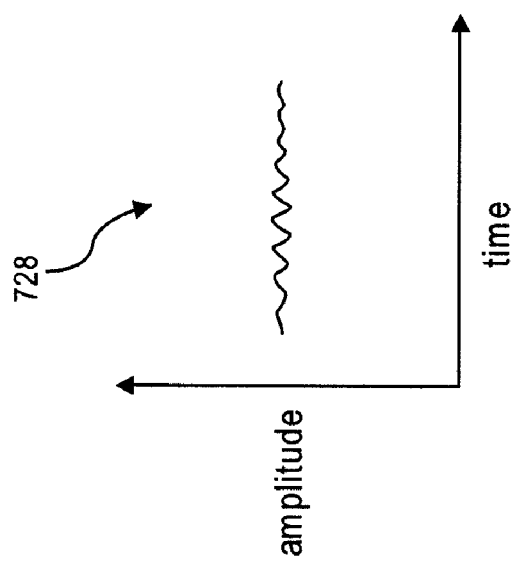

As the bubble 708 reaches the transducer 702, as shown in FIG. 7C, the amplitude of the signal detected at transducer 704 begins to attenuate sharply, as illustrated by reference number 724 (point C in FIG. 8). FIG. 7D illustrates the received signal 728 when the bubble 708 is traversing the central region of the sensor conduit 712 (point D in FIG. 8). These figures illustrate why a system for compensating for the presence of the bubble 708 is of value; in the absence of such a system, these transient changes in signal amplitude will appear to the control system as changes in flow rate for which the control system will attempt to compensate, which may result in unstable flow.

Figure 7E:
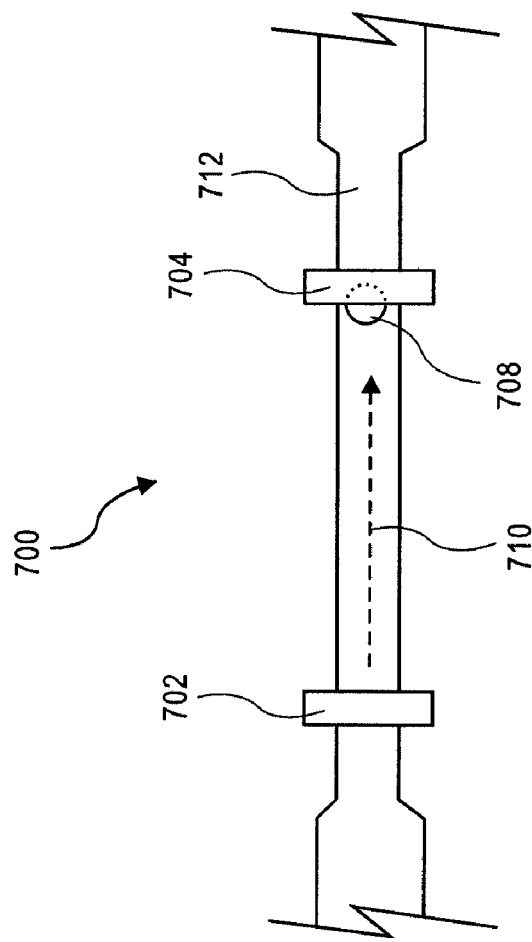
FIG. 7E illustrates a signal in an ultrasonic sensor conduit as a bubble reaches a second transducer.
Figure 7E:
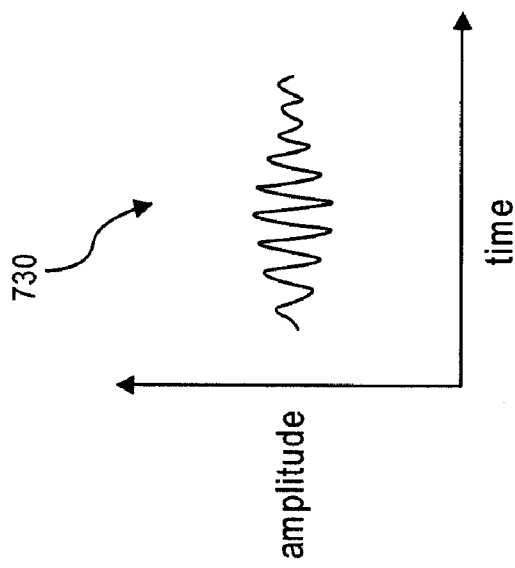
Figure 7F:
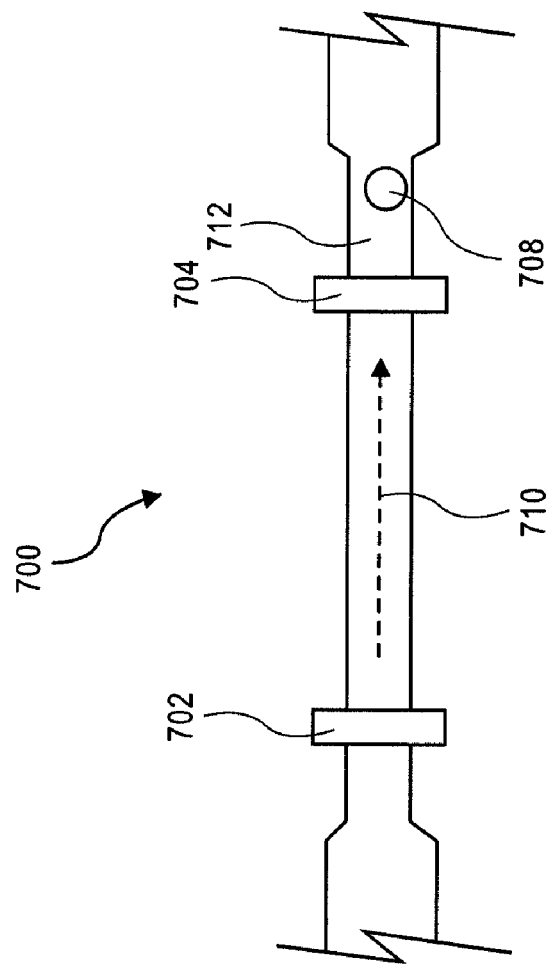
FIG. 7F illustrates a signal in an ultrasonic sensor conduit as a bubble reaches the exit end of the conduit.
Figure 7F:
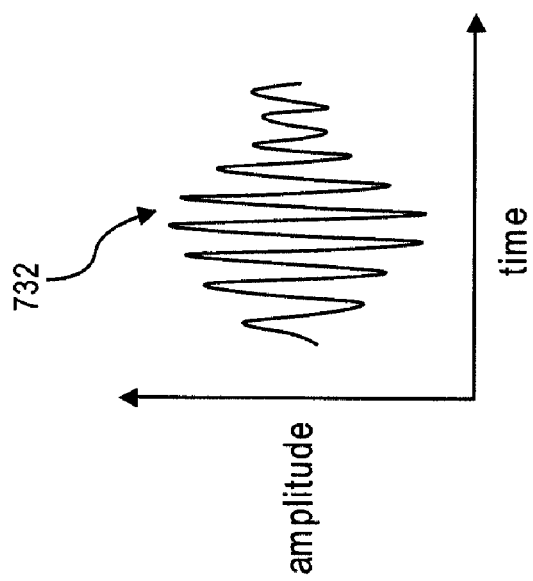
Figure 7G:
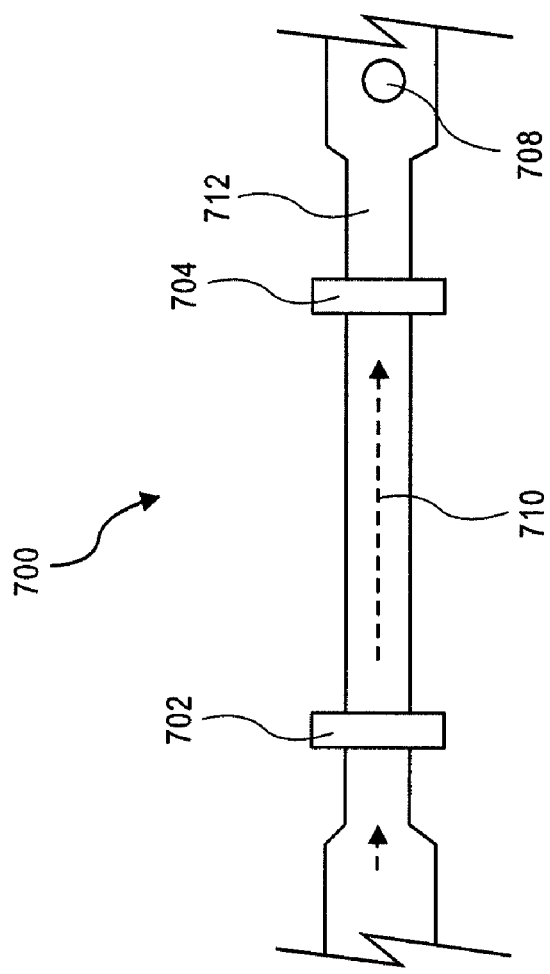
FIG. 7G illustrates a signal in an ultrasonic sensor conduit after a bubble has exited the sensor conduit.
Figure 7G:
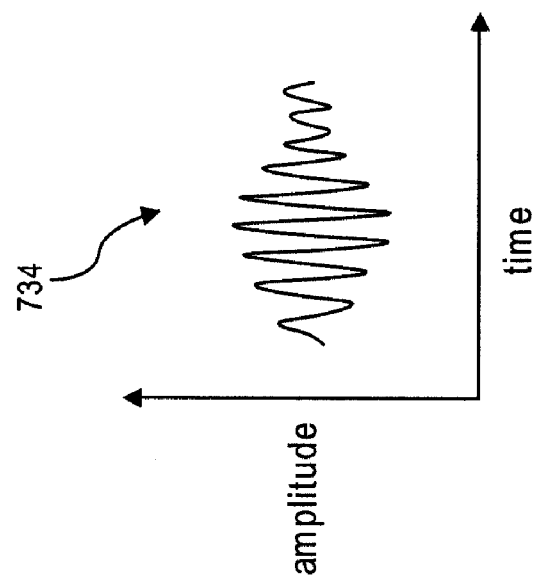

As the bubble 708 reaches and passes the transducer 704, as shown in FIG. 7E, the received signal 730 rises sharply (point E in FIG. 8). Generally, the signal level may overshoot before stabilizing to a steady state value. The overshoot may be attributed at least in part to the reinforcement in phases of the primary ultrasound wavefront traveling from the transducer 702 and the reflected wave from the bubble 708 as it reaches the transducer 704. The reflected signal fades away as the bubble 708 moves through the measurement section of the sensor conduit as shown in FIG. 7F (point F in FIG. 8). Finally, as shown in FIG. 7G, as the bubble 708 exits the sensor conduit 712, the received signal amplitude 734 returns to its steady state value (point G at FIG. 8).

An exemplary bubble detection process takes advantage of the characteristic time evolution of the detected signal amplitude, such as that illustrated in FIGS. 7A-7G and FIG. 8, to detect the presence of the bubble 708. It should be appreciated that the time evolution of the detected signal amplitude illustrated in FIGS. 7A-7G and FIG. 8 reflects measurements obtained with a particular flow sensor over a particular range of flow rates, and that the characteristic time evolution of the detected signal amplitude may vary when used with other sensor configurations and other flow rates. Empirical measurements may be made with other sensor configurations and at other flow rates to identify the manner in which the presence of a bubble can affect the detected signal amplitude, and a bubble detection process may then be adapted to reflect that characteristic signature.

Figure 4:
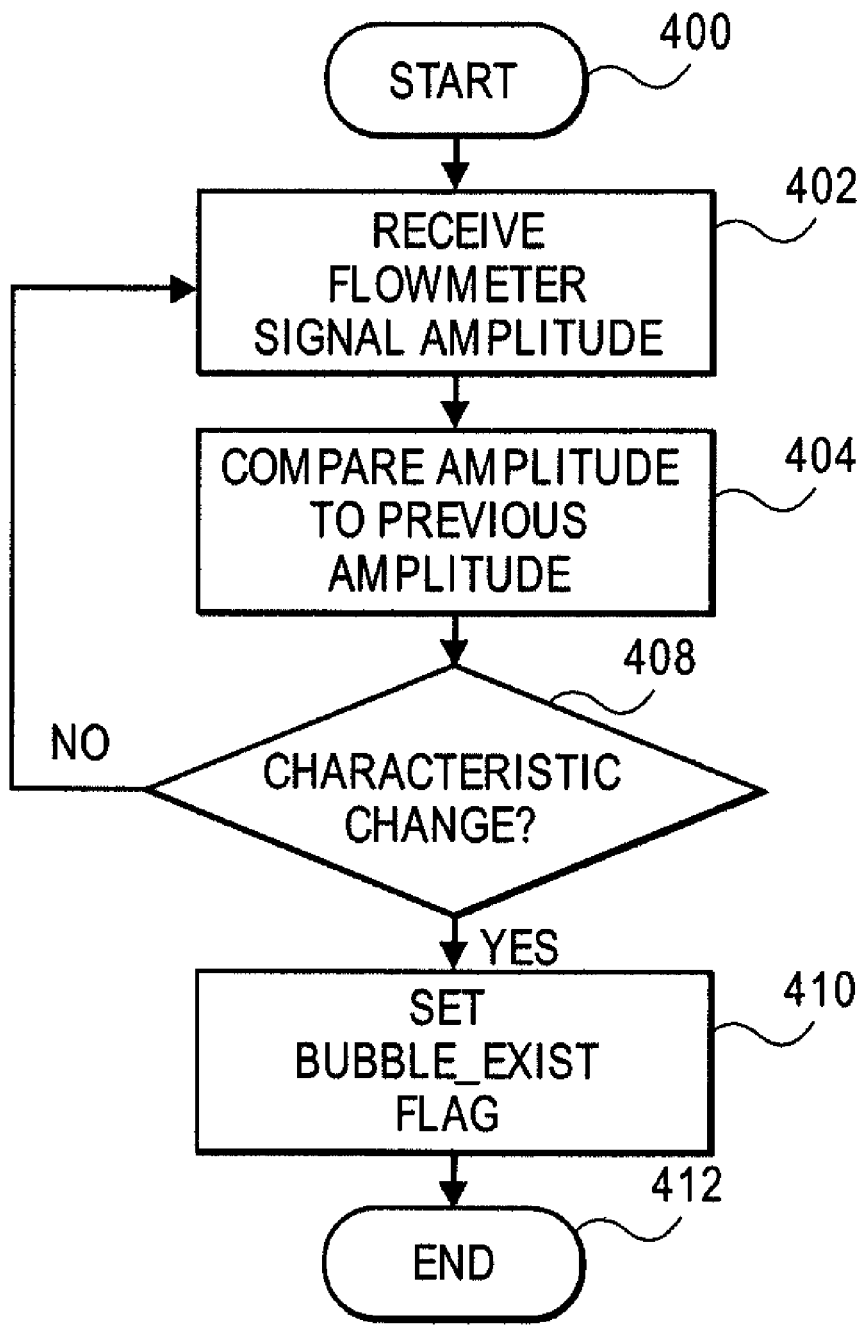
FIG. 4 is a flow diagram illustrating an exemplary embodiment of a method of detecting the presence of a bubble in the sensor conduit of a liquid flow system.

In accordance with the present invention, an exemplary bubble detection process, illustrated functionally in FIG. 4, is provided that compares successive detected signal amplitudes to previous signal amplitudes, looking for the characteristics indicative of the presence of a bubble, such as those illustrated in FIGS. 7A-7G and FIG. 8. In one exemplary embodiment, a bubble detection system may receive signal amplitude values from the flow meter (block 402). In one embodiment, a number of received signal amplitudes may be stored in a memory associated with the flow meter, the flow controller, or the bubble detection module. The system periodically compares the received amplitude to a previously received and stored amplitude or, alternatively, to multiple previously received and stored amplitudes (block 404). Where the system detects a characteristic change in signal amplitude (such as that illustrated in FIGS. 7A-7G and FIG. 8) (block 408), it may, in response, generate an alarm signal (block 410) as described above.

A further exemplary embodiment computes a weighted sum of the detected flow meter signal amplitude and, where the received value of the amplitude of the flow meter signal amplitude deviates from the weighted sum, for example, by some predetermined threshold or amount, sends in response a positive bubble detection signal. For example, the embodiment illustrated in FIG. 5 computes a running average of the detected ultrasonic signal amplitude and, where the received value of the amplitude of the flow meter signal deviates from the running average, sends in response a positive bubble detection signal. It should be appreciated that although a running average of the detected ultrasonic signal amplitude is used in this embodiment, other forms of weighted sums of the detected ultrasonic signal amplitude may be used, as the present invention is not so limited. For example, rather than simply computing a running average, more recently received values of the amplitude of the flow meter signal may be accorded a different (e.g., higher) weight than those that were received less recently. The weighted sum may be computed by a processor associated with the flow meter, the flow controller, or the bubble detection module, although it should be appreciated that such a weighted sum could alternatively be determined by filtering the received flow meter signals using, for example, a low pass filter.

Figure 5:
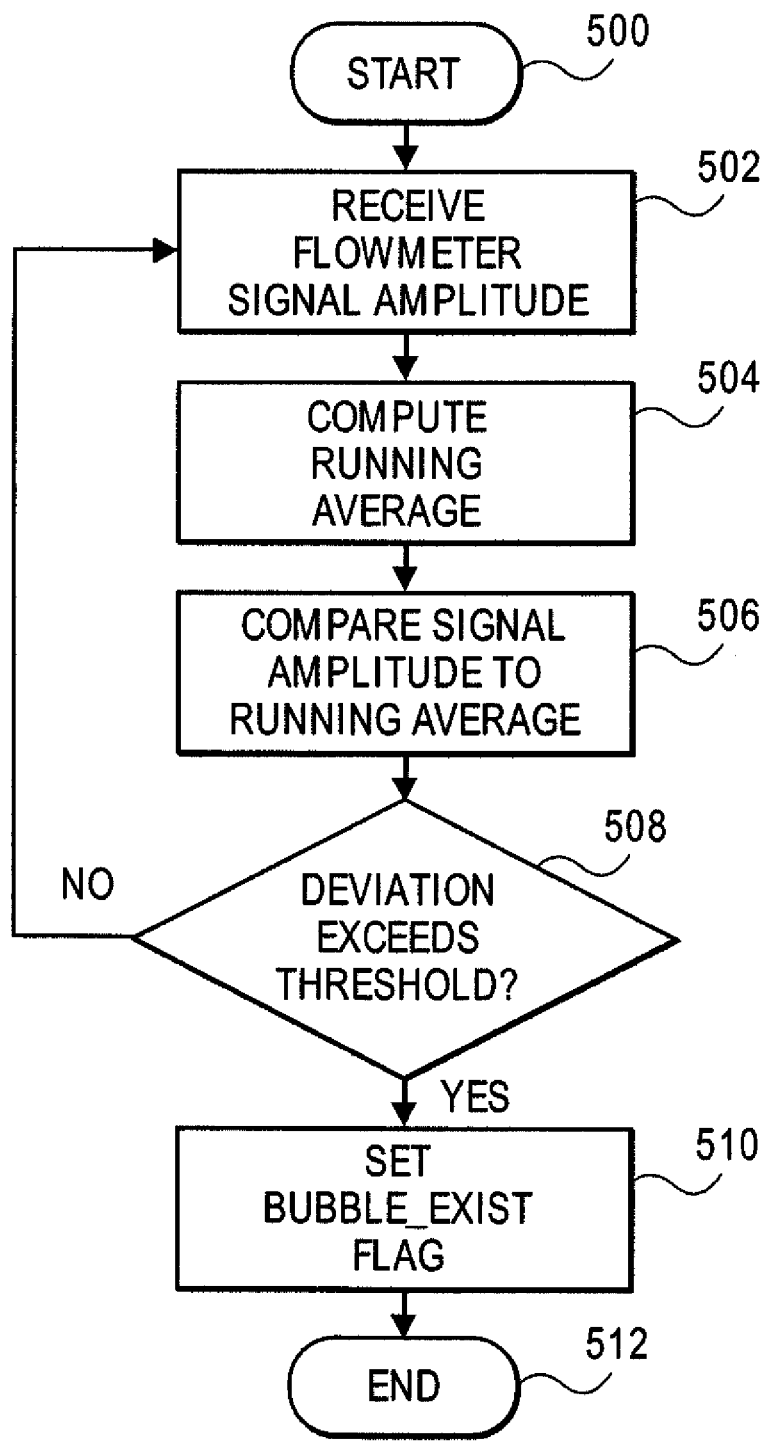
FIG. 5 is a flow diagram illustrating an exemplary embodiment of a method of detecting the presence of a bubble in the sensor conduit of a liquid flow system.

In accordance with the embodiment depicted in FIG. 5, the amplitude of the received signal may be periodically sampled and stored in a buffer (block 502), sampling the flow measurement at some predetermined time interval. Some number N of samples (e.g. 20 samples in one exemplary embodiment) may be stored. In one exemplary embodiment, the signal samples may be stored in a stack such that as the new received signal is sampled, the new data is placed on top and the old data is pushed down the stack. After the data is collected for the predetermined number of N samples, the average signal amplitude is calculated. An advantage of determining a running average amplitude in real time, rather than storing a preset value, is that different sensor configurations may lead to different signal strengths, depending upon the physical mountings of the sensors, the flow parameters in the particular arrangement, and other factors. Thus, while a predetermined value of the amplitude (i.e., determined during calibration, based upon measurements from similar sensors, etc.) may be employed as a reference, determining a running average signal amplitude in real-time is preferred.

As new samples are taken, the newest sample is stored at the top of the stack, and the oldest sample (at the bottom of the stack) is discarded. The running average of N samples in the buffer is calculated periodically (block 504). In an exemplary embodiment the running average signal amplitude may be computed each time a new sample is placed in the buffer.

In one exemplary embodiment, a threshold level window that extends above and below the running average value is selected as a bubble detection threshold, such that upon the received value of the amplitude of the flow meter signal exceeding this threshold or dipping below it, a bubble is presumed to have been detected and a positive bubble detection signal is generated (blocks 508, 510). The threshold may be selected to be some percentage deviation above and below the running average value. For example, the threshold may be a 10, 15, or 20 percent deviation from the running average value. The threshold value can be larger or smaller depending upon a number of system parameters and operating conditions. The threshold need not be symmetric about the running average value. Factors that contribute to the determination of the threshold value may include (without limitation) viscosity of the liquid whose flow is being measured, operating temperatures and pressure, particle contents when the liquid is a slurry, etc. In practice, an optimal threshold can be determined by trial and error or during calibration, for example, by deliberately injecting bubbles into the sensor conduit and setting a threshold level that allows the desired efficiency of bubble detection (i.e., minimizing the number of undetected bubbles and the number of false positives). The comparison of the received value of the amplitude of the flow meter signal to a threshold reduces the possibility of a false positive bubble detection.

In accordance with the embodiment depicted in FIG. 5, where the received amplitude value of the flow signal exceeds the upper threshold value or falls below the lower threshold value, the system in response generates a positive bubble-detection signal (block 508). In one exemplary embodiment, a positive bubble-detection signal may simply entail asserting a bubble-exist flag (i.e. setting a Boolean bubble-exist variable to some particular value). The bubble-exist flag may remain asserted until the bubble leaves the sensor conduit (or at least the measurement section of the sensor conduit). The bubble-exist flag can be used as a trigger signal for other control and data storage operations, such as freezing control parameters or freezing recorded measurement values, as described above.

In an exemplary embodiment, upon assertion of the bubble-exist flag, the system may, in response, start a timer that counts time (CPU clock cycles, or a number of process or thread cycles). This timer can be used to determine whether assertion of the bubble-exist flag is due to a true bubble being present, or to a momentary glitch in the data collection. That is, where the bubble-exist flag remains asserted for a time that is less than a predetermined minimum number of clock cycles or thread cycles, the system may, in response, treat the excursion beyond threshold as a glitch rather than a true bubble event. On the other hand, where the bubble-exist flag is asserted for a time longer than some predetermined maximum interval (or number of clock or thread cycles), it is likely that the bubble has blocked the sensor conduit and stopped the flow entirely. In such a circumstance, the system may, in response, initiate an action for the controlled forcing of the bubble to return the flow to the normal steady-state operating condition, as discussed above. The predetermined maximum interval (or number of cycles) at which a controlled forcing procedure may be initiated depends upon operating conditions such as flow rate, liquid viscosity, etc.

In some embodiments, it is desirable to detect the presence of a bubble very early in its transit through the sensor conduit. In particular, where the ultrasonic flow meter is used as the sensor component in a flow controller, it is desirable to detect the bubble as soon as possible before it disrupts the control signal, preferably before the controller has had a chance to alter the feedback parameters (and hence the flow rate) in response to the spurious signals caused by the presence of the bubble.

In some cases, the moving or running average threshold detection described above will sense the bubble in a timely manner, and the controller will respond to the positive bubble-detection signal, holding the controller parameters until the bubble completes its transit through the sensor conduit. However, as illustrated in FIG. 7b and at point B in FIG. 8, where the amplitude of the signal rises sharply, it can be beneficial to alert the controller about this signal spike early, before the running average signal amplitude (or some other weighted sum) reflects it, and before the control system reacts to the changes. One exemplary embodiment of a flow meter with bubble detection may therefore employ a differential threshold detection scheme that assists in detecting bubbles at very early stages, before the controller has committed to the change of operating parameters.

In one embodiment, the differential threshold detection is based on the change in the value of the time-of-flight delay difference parameter, denoted herein as $x_0$, which is more sensitive than the amplitude change. The time-of-flight delay difference parameter $x_0$ is the difference between the transit time of an ultrasonic signal (for example, a chirp signal) traveling from transducer 702 to transducer 704 and the transit time of an ultrasonic signal traveling in the reverse direction from transducer 704 to transducer 702 (that is, the difference between the downstream transit time and the upstream transit time). The difference between the current value $x_0[t]$ and a previous value $x_0[t-1]$ may be periodically computed and this resultant difference then compared to a predetermined threshold (blocks 608, 610).

Figure 9:
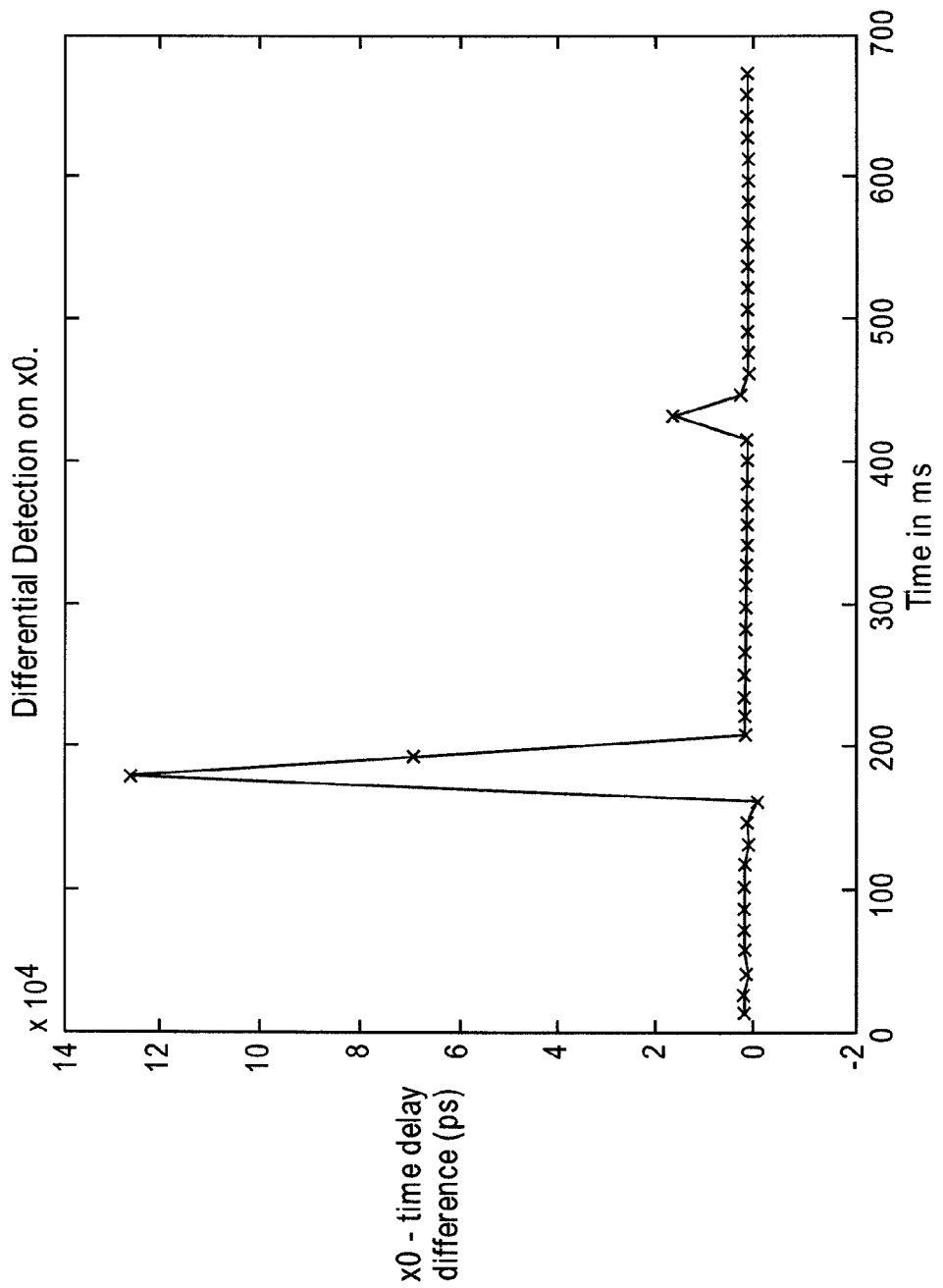
FIG. 9 illustrates a differential time-of-flight signal obtained from an ultrasonic flow sensor, plotted against time, as a bubble traverses the sensor conduit of the flow sensor.

FIG. 9 illustrates the corresponding plot of the time-of-flight difference values $x_0[t]-x_0[t-1]$ against time for the entire bubble transit sequence illustrated in FIGS. 7A-7G and 8. It can be seen from FIG. 9 that when using the $x_0$ differences, the presence of a bubble appears as a sharp spike very close to the beginning of the characteristic signal sequence observed in FIG. 8.

Figure 6:
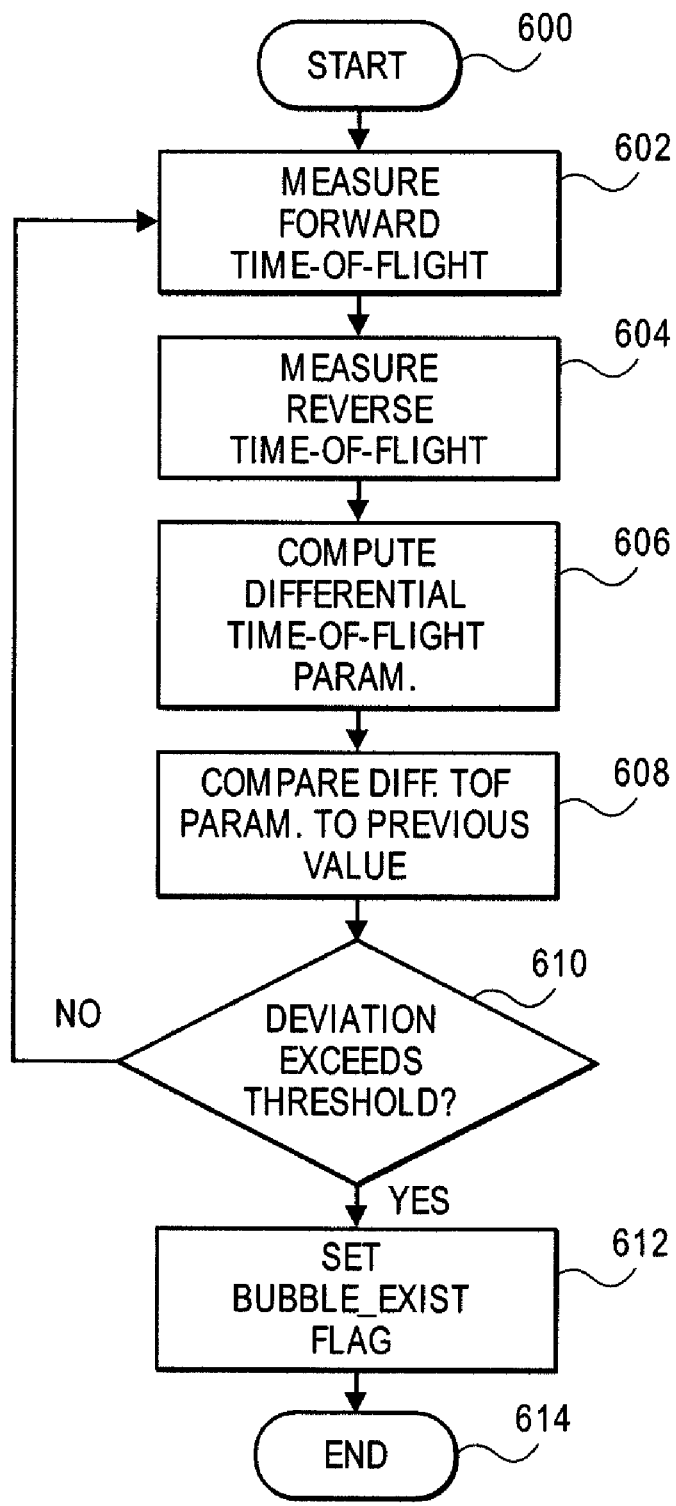
FIG. 6 is a flow diagram illustrating an exemplary embodiment of a method of detecting the presence of a bubble in the sensor conduit of a liquid flow system.

An exemplary embodiment of a bubble detection process employing such a differential measurement is illustrated functionally in FIG. 6. Values of the time-of-flight delay difference parameter $x_0$ may be computed periodically by measuring the downstream time-of-flight (block 602), measuring the upstream time-of-flight (block 604), and taking the difference (block 606). It should be appreciated that blocks 602 and 604 may be performed in the reverse order or simultaneously.

In one exemplary embodiment the time-of-flight difference $x_0[t]-x_0[t-1]$ is computed each time a new $x_0$ value is obtained. Upon a determination that the difference exceeds a predetermined threshold (the differential threshold), then a bubble is suspected and a positive bubble detection signal, such as asserting a bubble-exist flag, can be generated (blocks 610, 612). Alternatively, to minimize the incidence of false positive responses, the differential threshold condition may be checked again at the next thread cycle, and a positive bubble detection signal generated only where the threshold condition is again met. In either case, the threshold value may be selected to be greater than the maximum change in $x_0$ that could occur due to the step changes in system parameters such as set point values, so that false positive bubble-detection signals are not generated when the flow parameters are deliberately changed. Alternatively, differential bubble detection may be temporarily locked out or suspended during changes in setpoint values.

A positive bubble detection signal generated as a result of a change in $x_0$ that exceeds the differential threshold may be used as described above to freeze feedback parameters or measurement values, preventing destabilizing system response to spurious signals generated by the presence of the bubble.

The differential detection criterion may detect a bubble's presence earlier than running average detection, and therefore may provide an early warning, allowing the system to freeze the controller states before the controller states are corrupted by the spurious signals caused by the presence of the bubble. Even where the differential detection precedes running average detection by as little as one or two thread cycles, it can still be useful in facilitating stable operation of a control system during transit of a bubble.

In an exemplary embodiment, the differential detection supplements the running average detection described previously above, and is mainly active during the bubble's entry into the sensor conduit. However, it can also be used to detect the bubble's exit from the sensor conduit, as illustrated by the second, smaller peak in FIG. 9.

Although the present invention has been primarily described herein as being used to provide accurate measurement and/or control of fluid flow rate in the presence of bubbles, aspects of the present invention may be used for other purposes where the presence of bubble may affect a measurement and/or control process. For example, U.S. Pat. No. 5,569,844 describes the use of ultrasonic waves to measure the particle size and distribution of solids in a suspension of solids in solution, such as a CMP slurry. The '844 patent describes that the presence of bubbles can limit the accuracy of such measurements, and notes that bubbles typically need to be eliminated prior to measurement. Aspects of the present invention may be readily adapted to such a particle size and distribution measurement scheme to detect the presence of bubbles, and/or to limit particle size and distribution measurements to periods in which bubbles are not detected. Adaptations to other technologies where the presence of bubbles may impact measurement and/or control may also be readily envisioned.

Having thus described several aspects of embodiments of the present systems and methods for measuring and controlling liquid flow, it is to be appreciated various alterations, modifications, and improvements will readily occur to those skilled in the art. Such alterations, modifications, and improvements are intended to be part of this disclosure, and are intended to be within the scope of the invention. Accordingly, the foregoing description and drawings are by way of example only.

What is claimed is:

1. A method of measuring a flow rate of a liquid flowing in a liquid flow sensor, the liquid flow sensor including a sensor conduit and the liquid including a plurality of bubbles formed therein, the method comprising acts of:
   repeatedly sensing a flow signal indicative of the flow rate of the liquid flowing in the sensor conduit;
   calculating, responsive to the act of repeatedly sensing a weighted sum of a value of the at least one parameter of the flow signal;
   determining, based upon at least one parameter of the flow signal, whether at least one bubble is disposed in the liquid within the sensor conduit, wherein the act of determining includes an act of determining whether a most recently sensed value of the at least one parameter of the flow signal deviates from the weighted sum by more than a determined amount;
   providing, in response to a determination that no bubble is disposed in the liquid within the sensor conduit, a flow rate signal indicative of the flow rate of the liquid flowing in the liquid flow sensor based upon a most recently sensed flow signal; and
   providing, in response to a determination that the at least one bubble is disposed in the liquid within the sensor conduit, at least one of:

a) a flow rate signal based upon the most recently sensed flow signal and an alert signal indicative of a presence of the at least one bubble, and
b) a flow rate signal indicative of the flow rate of the liquid flowing in the liquid flow sensor based upon other than the most recently sensed flow signal.

2. The method of claim 1, wherein the act of determining includes an act of detecting at least one change in the at least one parameter of the flow signal, the change being characteristic of the presence of the at least one bubble disposed in the liquid within the sensor conduit.

3. The method of claim 1, wherein the liquid flow sensor comprises an ultrasonic liquid flow sensor.

4. The method of claim 3, wherein the at least one parameter of the flow signal comprises an ultrasonic flow signal amplitude.

5. The method of claim 4, wherein the act of determining includes an act of detecting a change in the ultrasonic flow signal amplitude, the change being characteristic of the presence of the at least one bubble disposed in the liquid within the sensor conduit.

6. The method of claim 5, further comprising an act of:
calculating, responsive to the act of repeatedly sensing, a running average of a value of the ultrasonic flow signal amplitude;
wherein the act of determining includes an act of determining whether a most recently sensed value of the ultrasonic flow signal amplitude deviates from the running average by more than a threshold value.

7. The method of claim 3, wherein the flow signal comprises an ultrasonic time-of-flight difference flow signal, and wherein the at least one parameter of the flow signal includes a magnitude of the ultrasonic time-of-flight difference flow signal.

8. The method of claim 7, wherein the act of determining includes an act of determining whether the magnitude of the ultrasonic time-of-flight difference flow signal deviates from the magnitude of a prior ultrasonic time-of-flight difference flow signal by more than a threshold value.

9. The method of claim 1, wherein the act of providing the flow rate signal indicative of the flow rate of the liquid flowing in the liquid flow sensor based upon other than the most recently sensed flow signal includes providing a previously sensed flow signal for which it was previously determined that no bubble was disposed in the liquid within the sensor conduit.

10. The method of claim 9, wherein the previously sensed flow signal comprises the most recently sensed flow signal for which it was previously determined that no bubble was disposed in the liquid within the sensor conduit.

11. The method of claim 1, wherein the act of providing the flow rate signal indicative of the flow rate of the liquid flowing in the liquid flow sensor based upon other than the most recently sensed flow signal includes providing a previously sensed flow signal for which it was previously determined that no bubble was disposed in the liquid within the sensor conduit along with the alert signal.

12. A method of controlling the flow rate of a liquid through a flow conduit coupled to a controllable valve and a liquid flow sensor, liquid flow sensor including a sensor conduit and the liquid including a plurality of bubbles formed therein, the method comprising acts of
repeatedly sensing a flow signal indicative of the flow rate of the liquid flowing in the sensor conduit;
determining, based upon at least one parameter of the flow signal, whether at least one bubble is disposed in the liquid within the sensor conduit;
providing, in response to a determination that no bubble is disposed in the liquid within the sensor conduit, control parameters for the controllable valve based upon the most recently sensed flow signal;
providing, in response to a determination that the at least one bubble is disposed in the liquid within the sensor conduit, control parameters for the controllable valve based upon other than the most recently sensed flow signal;
controlling the controllable valve according to the control parameters;
waiting a predetermined period of time in response to a determination that the at least one bubble is disposed in the liquid within the sensor conduit;
determining, after the predetermined period of time whether the at least one bubble is still disposed in the liquid within the sensor conduit based upon the at least one parameter of the flow signal; and
executing, in response to a determination that the at least one bubble is still disposed in the liquid within the sensor conduit, a controlled force procedure to remove the at least one bubble from the liquid within the sensor conduit.

13. The method of claim 12, wherein the act of determining includes detecting at least one change in the at least one parameter of the flow signal, the change being characteristic of a presence of the at least one bubble disposed in the liquid within the sensor conduit.

14. The method of claim 12, wherein the liquid flow sensor comprises an ultrasonic liquid flow sensor.

15. The method of claim 14, wherein the at least one parameter of the flow signal comprises an ultrasonic flow signal amplitude.

16. The method of claim 15, wherein the act of determining includes detecting a change in the ultrasonic flow signal amplitude, the change being characteristic of a presence of the at least one bubble disposed in the liquid within the sensor conduit.

17. The method of claim 16, further comprising an act of
calculating, responsive to the act of repeatedly sensing, a running average of a value of the ultrasonic flow signal amplitude;
wherein the act of determining includes an act of determining whether a most recently sensed value of the ultrasonic flow signal amplitude deviates from the running average by more than a threshold value.

18. The method of claim 14, wherein the flow signal comprises an ultrasonic time-of-flight difference flow signal, and wherein the at least one parameter of the flow signal includes a magnitude of the ultrasonic time-of-flight difference flow signal.

19. The method of claim 18, wherein the act of determining includes an act of determining whether the magnitude of the ultrasonic time-of-flight difference flow signal deviates from the magnitude of a prior ultrasonic time-of-flight difference flow signal by more than a threshold value.

20. The method of claim 12, further comprising an act of:
calculating, responsive to the act of repeatedly sensing, a weighted sum of a value of the at least one parameter of the flow signal;
wherein the act of determining includes an act of determining whether a most recently sensed value of the at least one parameter of the flow signal deviates from the weighted sum by more than a determined amount.

21. The method of claim 12, further comprising an act of:
calculating, responsive to the act of repeatedly sensing, a running average of a value of the at least one parameter of the flow signal;
wherein the act of determining includes an act of determining whether a most recently sensed value of the at least one parameter of the flow signal deviates from the running average by more than a threshold value.

22. The method of claim 12, wherein the act of providing control parameters based upon other than the most recently sensed flow signal includes providing previously provided control parameters for which it was determined that no bubble was disposed in the liquid within the sensor conduit.

23. The method of claim 22, wherein the previously provided control parameters comprise the most recently provided control parameters for which it was previously determined that no bubble was disposed in the liquid within the sensor conduit.

24. The method of claim 12, wherein the act of determining whether the at least one bubble is still disposed in the liquid within the sensor conduit includes detecting at least one change in the at least one parameter of the flow signal, the change being characteristic of one of:
a) a presence of the at least one bubble disposed in the liquid within the sensor conduit; and
b) an exit of the at least one bubble from the liquid within the sensor conduit.

25. The method of claim 12, wherein the act of executing a controlled force procedure includes temporarily altering the control parameters for the controllable valve.

26. The method of claim 12, wherein the act of executing a controlled force procedure includes opening and shutting the controllable valve.

27. A system for measuring a flow rate of a liquid flowing in a flow conduit, the liquid including a plurality of bubbles formed therein, the system comprising:
a liquid flow sensor including a sensor conduit fluidly coupled to the flow conduit, the liquid flow sensor being configured to sense a flow rate of the liquid flowing in the sensor conduit and provide a flow signal indicative of the flow rate of the liquid flowing in the sensor conduit;
a bubble detection module, coupled to the liquid flow sensor, to receive the flow signal and determine, based upon at least one parameter of the flow signal, whether at least one bubble is disposed in the liquid within the sensor conduit, the bubble detection module being configured to:
provide, in response to a determination that no bubble is disposed in the liquid within the sensor conduit, a flow rate signal indicative of the flow rate of the liquid flowing in the liquid flow sensor based upon a most recently sensed flow signal, and provide, in response to a determination that the at least one bubble is disposed in the liquid within the sensor conduit, at least one of:
a) a flow rate signal based upon the most recently sensed flow signal and an alert signal indicative of a presence of the at least one bubble, and
b) a flow rate signal indicative of the flow rate of the liquid flowing in the liquid flow sensor based upon other than the most recently sensed flow signal, wherein the flow rate signal indicative of the flow rate of the liquid flowing in the liquid flow sensor based upon other than the most recently sensed flow signal comprises a previously sensed flow rate signal for which it was previously determined that no bubble was disposed in the liquid within the sensor conduit.

28. The system of claim 27, wherein the bubble detection module detects at least one change in the at least one parameter of the flow signal, the change being characteristic of the presence of the at least one bubble disposed in the liquid within the sensor conduit.

29. The system of claim 27, wherein the liquid flow sensor comprises an ultrasonic liquid flow sensor.

30. The system of claim 29, wherein the at least one parameter of the flow signal comprises an ultrasonic flow signal amplitude.

31. The system of claim 30, wherein the bubble detection module detects a change in the ultrasonic flow signal amplitude, the change being characteristic of the presence of the at least one bubble disposed in the liquid within the sensor conduit.

32. The system of claim 31, wherein the bubble detection module is further configured to:
calculate a running average of a value of the ultrasonic flow signal amplitude; and
determine whether a most recently sensed value of the ultrasonic flow signal amplitude deviates from the running average by more than a threshold value.

33. The system of claim 29, wherein the flow signal comprises an ultrasonic time-of-flight difference flow signal, and wherein the at least one parameter of the flow signal includes a magnitude of the ultrasonic time-of-flight difference flow signal.

34. The system of claim 33, wherein the bubble detection module is further configured to:
determine whether the ultrasonic time-of-flight difference flow signal deviates from a previously determined ultrasonic time-of-flight difference flow signal by more than a detection threshold value.

35. The system of claim 27, wherein the bubble detection module is further configured to:
calculate a weighted sum of a value of the at least one parameter of the flow signal; and
determine whether the most recently sensed value of the at least one parameter of the flow signal deviates from the weighted sum by more than a determined amount.

36. The system of claim 27, wherein the bubble detection module is further configured to:
calculate a running average of a value of the at least one parameter of the flow signal; and
determine whether the most recently sensed value of the at least one parameter of the flow signal deviates from the running average by more than a threshold value.

37. The system of claim 27, wherein the previously sensed flow rate signal comprises the most recently sensed flow rate signal for which it was previously determined that no bubble was disposed in the liquid within the sensor conduit.

38. The system of claim 27, further comprising:
a controllable valve in fluid communication with the flow conduit, to control the flow rate of the fluid flowing in the flow conduit based upon control parameters provided to the controllable valve; and
a controller, coupled to the liquid flow sensor and the controllable valve, to receive the flow signal from the liquid flow sensor and provide the control parameters to the controllable valve.

39. The system of claim 38, wherein:
the bubble detection module is implemented in the controller;
wherein, upon the determination that no bubble is disposed in the liquid within the sensor conduit, the controller provides the control parameters to the controllable valve based upon the most recently sensed flow signal; and wherein, upon a determination that the at least one bubble is disposed in the liquid within the sensor conduit, the controller provides the control parameters to the controllable valve based upon other than the most recently sensed flow signal.

40. The system of claim 27, wherein the bubble detection module provides the flow rate signal based upon the most recently sensed flow signal and the alert signal indicative of the presence of the at least one bubble in response to the determination that the at least one bubble is disposed in the liquid with the sensor conduit, the system further comprising:
   a controllable valve in fluid communication with the flow conduit, to control the flow rate of the fluid flowing in the flow conduit based upon control parameters provided to the controllable valve; and
   a controller, coupled to the bubble detection module, to receive the flow rate signal and the alert signal and provide the control parameters to the controllable valve.

41. The system of claim 40, wherein:
   in response to the alert signal, the controller freezes the control parameters provided to the controllable valve at a prior value.

42. The system of claim 40, wherein:
   in response to the alert signal, the controller is configured to wait for a predetermined period of time, and upon a determination that the at least one bubble is still disposed in the liquid within the sensor conduit and the predetermined period of time has elapsed, implement a controlled force procedure to remove the at least one bubble from the liquid within the sensor conduit.

43. The system of claim 42, wherein the controlled force procedure comprises opening and shutting the controllable valve.

44. A method of measuring a flow rate of a liquid flowing in a liquid flow sensor, the liquid flow sensor including a sensor conduit and the liquid including a plurality of bubbles formed therein, the method comprising acts of:
   repeatedly sensing a flow signal indicative of the flow rate of the liquid flowing in the sensor conduit;
   calculating, responsive to the act of repeatedly sensing, a running average of a value of the at least one parameter of the flow signal;
   determining, based upon at least one parameter of the flow signal, whether at least one bubble is disposed in the liquid within the sensor conduit, wherein the act of determining includes an act of determining whether a most recently sensed value of the at least one parameter of the flow signal deviates from the running average by more than a threshold value;
   providing, in response to a determination that no bubble is disposed in the liquid within the sensor conduit, a flow rate signal indicative of the flow rate of the liquid flowing in the liquid flow sensor based upon a most recently sensed flow signal; and
   providing, in response to a determination that the at least one bubble is disposed in the liquid within the sensor conduit, at least one of:
      a) a flow rate signal based upon the most recently sensed flow signal and an alert signal indicative of a presence of the at least one bubble, and
      b) a flow rate signal indicative of the flow rate of the liquid flowing in the liquid flow sensor based upon other than the most recently sensed flow signal.

45. A system for measuring a flow rate of a liquid flowing in a flow conduit, the liquid including a plurality of bubbles formed therein, the system comprising:
   a liquid flow sensor including a sensor conduit fluidly coupled to the flow conduit, the liquid flow sensor being configured to sense a flow rate of the liquid flowing in the sensor conduit and provide a flow signal indicative of the flow rate of the liquid flowing in the sensor conduit;
   a bubble detection module, coupled to the liquid flow sensor, to receive the flow signal and determine, based upon at least one parameter of the flow signal, whether at least one bubble is disposed in the liquid within the sensor conduit, the bubble detection module being configured to:
   provide, in response to a determination that no bubble is disposed in the liquid within the sensor conduit, a flow rate signal indicative of the flow rate of the liquid flowing in the liquid flow sensor based upon a most recently sensed flow signal, and provide, in response to a determination that the at least one bubble is disposed in the liquid within the sensor conduit, at least one of:
      a) a flow rate signal based upon the most recently sensed flow signal and an alert signal indicative of a presence of the at least one bubble, and
      b) a flow rate signal indicative of the flow rate of the liquid flowing in the liquid flow sensor based upon other than the most recently sensed flow signal,
   a controllable valve in fluid communication with the flow conduit, to control the flow rate of the fluid flowing in the flow conduit based upon control parameters provided to the controllable valve; and
   a controller, coupled to the bubble detection module, to receive the flow rate signal and the alert signal and provide the control parameters to the controllable valve.

* * * * *